(12) United States Patent
Berndt et al.

(10) Patent No.: US 8,981,156 B2
(45) Date of Patent: *Mar. 17, 2015

(54) METHOD FOR PRODUCTION OF F-18 LABELED AMYLOID BETA LIGANDS

(75) Inventors: Mathias Berndt, Berlin (DE); Matthias Friebe, Berlin (DE); Christina Hultsch, Berlin (DE); Fabrice Samson, Ettingen (CH); Marianne Patt, Leipzig (DE); Andreas Schildan, Leipzig (DE); Christoph Smuda, Schlieren (CH)

(73) Assignee: Piramal Imaging SA, Matran (CH)

( * ) Notice: Subject to any disclaimer, the term of this patent is extended or adjusted under 35 U.S.C. 154(b) by 30 days.

This patent is subject to a terminal disclaimer.

(21) Appl. No.: 13/701,595

(22) PCT Filed: May 30, 2011

(86) PCT No.: PCT/EP2011/058786
§ 371 (c)(1),
(2), (4) Date: Mar. 18, 2013

(87) PCT Pub. No.: WO2011/151273
PCT Pub. Date: Dec. 8, 2011

(65) Prior Publication Data
US 2013/0172620 A1 Jul. 4, 2013

(30) Foreign Application Priority Data
Jun. 4, 2010 (EP) .................................. 10164950

(51) Int. Cl.
*C07D 213/64* (2006.01)
*C07C 213/08* (2006.01)
*C07D 213/63* (2006.01)
(Continued)

(52) U.S. Cl.
CPC .............. *C07D 213/64* (2013.01); *A61K 51/04* (2013.01); *C07B 59/00* (2013.01); *C07D 213/63* (2013.01); *C07C 213/08* (2013.01)
USPC ........................... 564/437; 546/300; 564/442

(58) Field of Classification Search
CPC .. C07D 213/64; C07D 213/63; C07C 213/08; C07B 59/00; A61K 51/00; A61K 51/04
USPC .................................. 564/442, 437; 546/300
See application file for complete search history.

(56) References Cited

U.S. PATENT DOCUMENTS

2010/0113763 A1* 5/2010 Moon et al. ................. 536/28.54
2010/0172836 A1* 7/2010 Benedum et al. ............ 424/1.89
2010/0292478 A1* 11/2010 Cho et al. ........................ 546/95

(Continued)

FOREIGN PATENT DOCUMENTS

WO     2011/003591 A1    1/2011

OTHER PUBLICATIONS

Zhang et. al. "18F-labeled styrylpyridines as PET agents for amyloid plaque imaging" Nuclear Medicine and Biology 34 (2007), p. 89-97.*

(Continued)

*Primary Examiner* — Fereydoun G Sajjadi
*Assistant Examiner* — Amy C Bonaparte
(74) *Attorney, Agent, or Firm* — Millen, White, Zelano & Branigan, P.C.

(57) ABSTRACT

This invention relates to methods, which provide access to [F-18]fluoropegylated (aryl/heteroaryl vinyl)-phenyl methyl amine derivatives.

15 Claims, 12 Drawing Sheets

(51) Int. Cl.
  *C07B 59/00* (2006.01)
  *A61K 51/04* (2006.01)

(56) References Cited

U.S. PATENT DOCUMENTS

2011/0137063 A1* 6/2011 Srinivasan et al. ............... 558/49
2012/0184749 A1   7/2012 Siebeneicher et al.

OTHER PUBLICATIONS

Sadek "The HPLC Solvent Guide" Wiley, 2nd edition, 2002, 664 pages.*
Krasikova "Synthesis Modules and Automation in F-18 Labeling" p. 289-316 of PET-Chemistry—The Driving Force in Molecular Imaging (2006), Springer, 348 p.*
International Search Report for PCT/EP2011/058786 (Sep. 26, 2011).
International Preliminary Report on Patentability for PCT/EP2011/058786 (Dec. 4, 2012).
C.H. Yao et al., "GMP-Compliant Automated Synthesis of [18F]AV-45 (Florbetapir F 18) for Imaging β-Amyloid Plaques in Human Brain", Applied Radiation and Isotopes, vol. 68, No. 12 (2010) pp. 2293-2297.
W. Zhang et al., "F-18 Polyethyleneglycol Stilbenes as PET Imaging Agents Targeting Aβ Aggregates in the Brain", Nuclear Medicine and Biology, vol. 32, No. 8 (2005) pp. 799-809.
Office Action for related Eurasian Patent Application No. 201201644 dated Feb. 6, 2014.
English Translation of Office Action for related Eurasian Patent Application No. 201201644 dated Feb. 6, 2014.

* cited by examiner

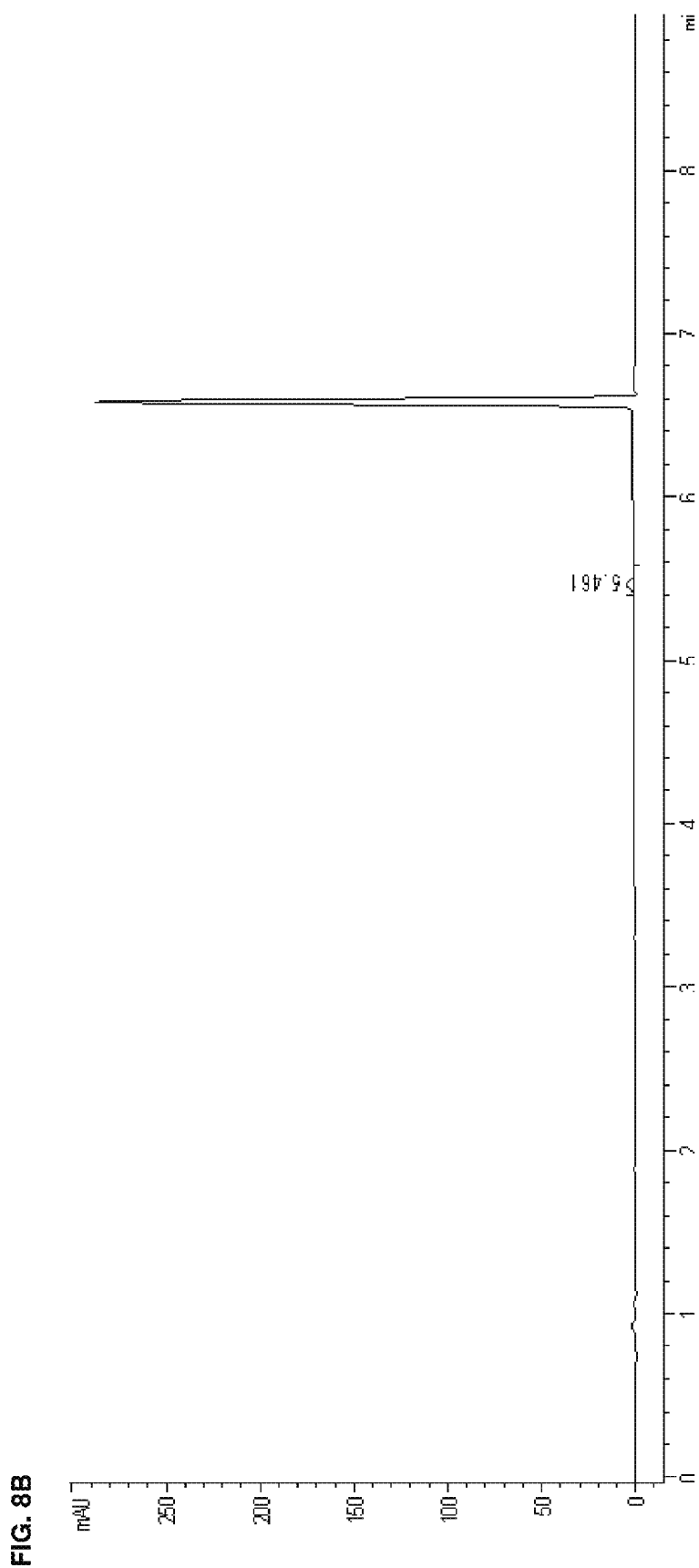

METHOD FOR PRODUCTION OF F-18 LABELED AMYLOID BETA LIGANDS

FIELD OF INVENTION

This invention relates to methods, which provide access to [F-18]fluoropegylated (aryl/heteroaryl vinyl)-phenyl methyl amine derivatives.

BACKGROUND

Alzheimer's Disease (AD) is a progressive neurodegenerative disorder marked by loss of memory, cognition, and behavioral stability. AD is defined pathologically by extracellular senile plaques comprised of fibrillar deposits of the beta-amyloid peptide (Aβ) and neurofibrillary tangles comprised of paired helical filaments of hyperphosphorylated tau. The 39-43 amino acids comprising Aβ peptides are derived from the larger amyloid precursor protein (APP). In the amyloidogenic pathway, Aβ peptides are cleaved from APP by the sequential proteolysis by beta- and gamma-secretases. Aβ peptides are released as soluble proteins and are detected at low level in the cerebrospinal fluid (CSF) in normal aging brain. During the progress of AD the Aβ peptides aggregate and form amyloid deposits in the parenchyma and vasculature of the brain, which can be detected post mortem as diffuse and senile plaques and vascular amyloid during histological examination (for a recent review see: Blennow et al. Lancet. 2006 Jul. 29; 368(9533):387-403).

Alzheimers disease (AD) is becoming a great health and social economical problem all over the world. There are great efforts to develop techniques and methods for the early detection and effective treatment of the disease. Currently, diagnosis of AD in an academic memory-disorders clinic setting is approximately 85-90% accurate (Petrella J R et al. Radiology. 2003 226:315-36). It is based on the exclusion of a variety of diseases causing similar symptoms and the careful neurological and psychiatric examination, as well as neuropsychological testing.

Molecular imaging has the potential to detect disease progression or therapeutic effectiveness earlier than most conventional methods in the fields of neurology, oncology and cardiology. Among the several promising molecular imaging technologies, such as optical imaging, MRI, SPECT and PET, PET is of particular interest for drug development because of its high sensitivity and ability to provide quantitative and kinetic data.

For example positron emitting isotopes include e.g. carbon, iodine, nitrogen, and oxygen. These isotopes can replace their non-radioactive counterparts in target compounds to produce PET tracers that have similar biological properties. Among these isotopes F-18 is a preferred labeling isotope due to its half life of 110 min, which permits the preparation of diagnostic tracers and subsequent study of biochemical processes. In addition, its low β+ energy (634 keV) is also advantageous.

Post-mortem histological examination of the brain is still the only definite diagnosis of Alzheimer's disease. Thus, the in vivo detection of one pathological feature of the disease—the amyloid aggregate deposition in the brain—is thought to have a strong impact on the early detection of AD and differentiating it from other forms of dementia. Additionally, most disease modifying therapies which are in development are aiming at lowering of the amyloid load in the brain. Thus, imaging the amyloid load in the brain may provide an essential tool for patient stratification and treatment monitoring (for a recent review see: Nordberg. Eur J Nucl Med Mol. Imaging. 2008 March; 35 Suppl 1:S46-50).

In addition, amyloid deposits are also known to play a role in amyloidoses, in which amyloid proteins (e.g. tau) are abnormally deposited in different organs and/or tissues, causing disease. For a recent review see Chiti et al. Annu Rev Biochem. 2006; 75:333-66.

Fluoropegylated (aryl/heteroaryl vinyl)-phenyl methyl amines such as 4-[(E)-2-(4-{2-[2-(2-fluoroethoxy)ethoxy]ethoxy}phenyl)vinyl]-N-methylaniline and 4-[(E)-2-(6-{2-[2-(2-fluoroethoxy)ethoxy]ethoxy}pyridin-3-yl)vinyl]-N-methylaniline have been labeled with F-18 fluoride and are covered by patent applications WO2006066104, WO2007126733 and members of the corresponding patent families.

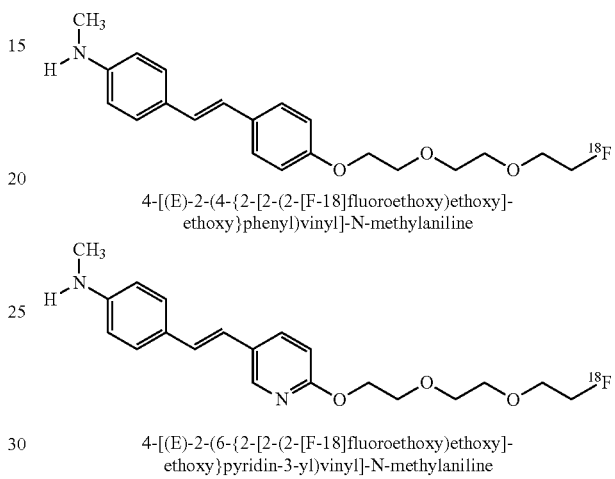

4-[(E)-2-(4-{2-[2-(2-[F-18]fluoroethoxy)ethoxy]ethoxy}phenyl)vinyl]-N-methylaniline 4-[(E)-2-(6-{2-[2-(2-[F-18]fluoroethoxy)ethoxy]ethoxy}pyridin-3-yl)vinyl]-N-methylaniline The usefulness of this radiotracers for the detection of Aβ plaques have been reported in the literature (W. Zhang et al., Nuclear Medicine and Biology 32 (2005) 799-809; C. Rowe et al., Lancet Neurology 7 (2008) 1-7; S. R. Choi et al., The Journal of Nuclear Medicine 50 (2009) 1887-1894).

To not limit the use of such F-18 labeled diagnostics, processes are needed, that allow a robust and safe manufacturing of the F-18 labeled tracers. Additionally, such processes should provide high yield of the overall synthesis to allow the production of quantities of the diagnostic to supply the radiotracer, despite of the half life of 110 min, to facilities without cyclotron or radiopharmaceutical production facility.

Syntheses of F-18 labeled fluoropegylated (aryl/heteroaryl vinyl)-phenyl methyl amines starting from commonly used mesylate and tosylate precursors have been described before:

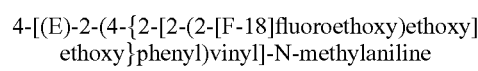

4-[(E)-2-(4-{2-[2-(2-[F-18]fluoroethoxy)ethoxy]ethoxy}phenyl)vinyl]-N-methylaniline

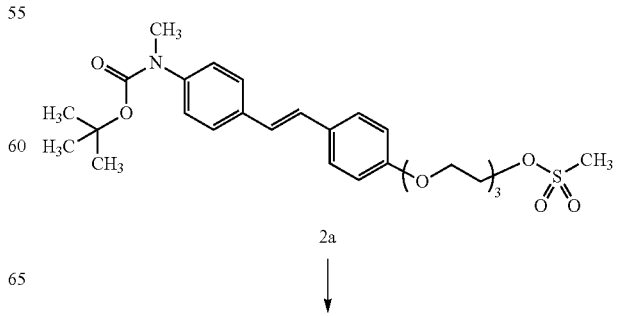

2a

-continued

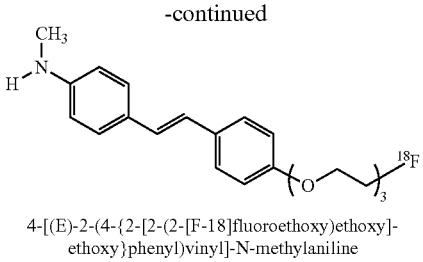

4-[(E)-2-(4-{2-[2-(2-[F-18]fluoroethoxy)ethoxy]-ethoxy}phenyl)vinyl]-N-methylaniline a) W. Zhang et al., Nuclear Medicine and Biology 32 (2005) 799-809

4 mg precursor 2a (2-[2-(2-{4-[(E)-2-{4-[(tert-butoxycarbonyl)(methyl)amino]-phenyl}vinyl]phenoxy}ethoxy)ethoxy]ethyl methanesulfonate) in 0.2 mL DMSO were reacted with [F-18]fluoride/kryptofix/potassium carbonate complex. The intermediate was deprotected with HCl and neutralized with NaOH. The mixture was extracted with ethyl acetate. The solvent was dried and evaporated. The residue was dissolved in acetonitrile and purified by semi-preparative HPLC. 20% (decay corrected), 11% (not corrected for decay) 4-[(E)-2-(4-{2-[2-(2-[F-18]fluoroethoxy)ethoxy]ethoxy}phenyl)vinyl]-N-methylaniline were obtained within 90 min.

b) WO2006066104

4 mg precursor 2a (2-[2-(2-{4-[(E)-2-{4-[(tert-butoxycarbonyl)(methyl)amino]-phenyl}vinyl]phenoxy}ethoxy)ethoxy]ethyl methanesulfonate) in 0.2 mL DMSO were reacted with [F-18]fluoride/kryptofix/potassium carbonate complex. The intermediate was deprotected with HCl and neutralized with NaOH. The mixture was extracted with ethyl acetate. The solvent was dried and evaporated, the residue was dissolved in acetonitrile and purified by semi-preparative HPLC. 30% (decay corrected), 17% (not corrected for decay) 4-[(E)-2-(4-{2-[2-(2-[F-18]fluoroethoxy)ethoxy]ethoxy}phenyl)vinyl]-N-methylaniline were obtained in 90 min.

c) US20100113763

2a (2-[2-(2-{4-[(E)-2-{4-[(tert-butoxycarbonyl)(methyl)amino]phenyl}vinyl]-phenoxy}ethoxy)ethoxy]ethyl methanesulfonate) was reacted with [F-18]fluoride reagent in a mixture of 500 μL tert-alcohol and 100 μL acetonitrile. After fluorination, the solvent was evaporated and a mixture of HCl and acetonitrile was added. After deprotection (heating at 100-120° C.), the crude product mixture was purified by HPLC (C18, 60% acetonitrile, 40% 0.1M ammonium formate).

4-[(E)-2-(6-{2-[2-(2-[F-18]-fluoroethoxy)ethoxy]ethoxy}pyridin-3-vinyl]-N-methylaniline

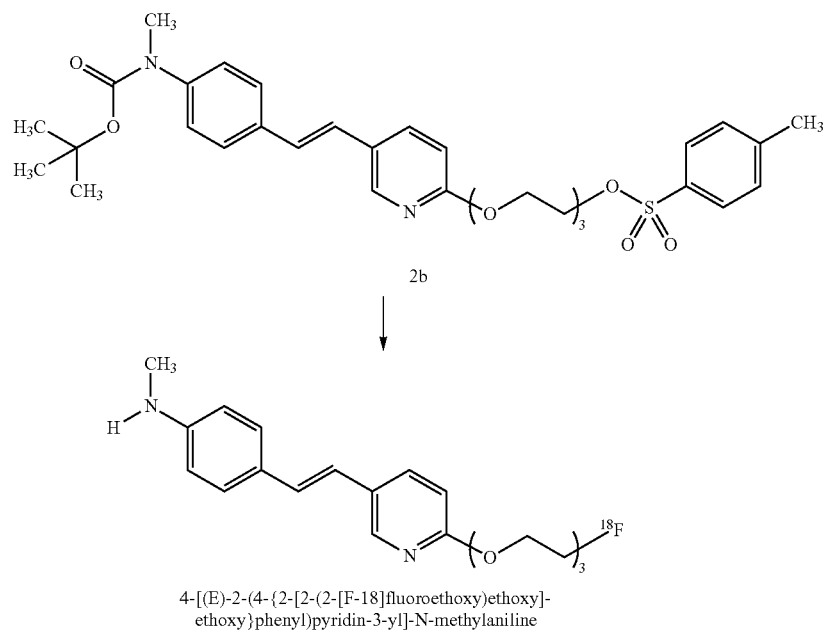

4-[(E)-2-(4-{2-[2-(2-[F-18]fluoroethoxy)ethoxy]-ethoxy}phenyl)pyridin-3-yl]-N-methylaniline a) S. R. Choi et al., The Journal of Nuclear Medicine 50 (2009) 1887-1894.

1 mg precursor 2b (2-{2-[2-({5-[(E)-2-{4-[(tert-butoxycarbonyl)(methyl)amino]-phenyl}vinyl]pyridin-2-yl}oxy)ethoxy]ethoxy}ethyl 4-methylbenzenesulfonate) in 1 mL DMSO was reacted with [F-18] fluoride/kryptofix/potassium carbonate complex. The intermediate was deprotected with HCl and neutralized with NaOH. DMSO and inorganic components were removed by solid-phase-extraction on SepPak light C18 cartridge (Waters). The crude product was purified by semi-preparative HPLC. The product fraction was diluted with water and passed through a SepPak light C18 cartridge. The radiotracer was eluted with ethanol. The yield for 4-[(E)-2-(6-{2-[2-(2-[F-18]fluoroethoxy)ethoxy]ethoxy}pyridin-3-yl)vinyl]-N-methylaniline was 10-30% (decay corrected).

WO2010000409 discloses a non-standard perfluorinated precursor for 4-[(E)-2-(4-{2-[2-(2-[F-18]fluoroethoxy)ethoxy]ethoxy}phenyl)vinyl]-N-methylaniline. It was demonstrated, that after radiolabeling with 1.3 GBq [F-18]fluoride an excess of 4.4 μmol precursor can be removed by solid-phase extraction on a perfluorinated stationary phase. However, the yield of the radiolabeled intermediate is only 24% and deprotection as well as final purification to obtain a composition, suitable for injection into patient is not disclosed. Furthermore is remains unclear if the process described is suitable for up-scaling to higher levels of radioactivity needed for commercial production (e.g. >50 GBq). Therefore, the focus of the present invention is towards a method wherein standard precursors such as mesylates and tosylates can be used, higher yields are obtained and scale-up is feasible.

Recently, further procedures for the syntheses of F-18 labeled fluoropegylated (aryl/heteroaryl vinyl)-phenyl methyl amines starting from commonly used mesylate and tosylate precursors have been described:

a) H. Wang et al., Nuclear Medicine and Biology 38 (2011) 121-127

5 mg precursor 2a (2-[2-(2-{4-[(E)-2-{4-[(tert-butoxycarbonyl)(methyl)amino]-phenyl}vinyl]phenoxy}ethoxy)ethoxy]ethyl methanesulfonate) in 0.5 mL DMSO were reacted with [F-18]fluoride/kryptofix/potassium carbonate complex. The intermediate was deprotected with HCl and neutralized with NaOH. The crude product was diluted with acetonitrile/0.1M ammonium formate (6/4) and purified by semi-preparative HPLC. The product fraction was collected, diluted with water, passed through a C18 cartridge and eluted with ethanol, yielding 17% (not corrected for decay) 4-[(E)-2-(4-{2-[2-(2-[F-18]fluoroethoxy)ethoxy]ethoxy}phenyl)vinyl]-N-methylaniline within 50 min. In the paper, the conversion of an unprotected mesylate precursor (is described:

5 mg unprotected mesylate precursor (2-{2-[2-(4-{(E)-2-[4-(methylamino)phenyl]vinyl}phenoxy)ethoxy]-ethoxy}ethyl 4-methanesulfonate) in 0.5 mL DMSO were reacted with [F-18]fluoride/kryptofix/potassium carbonate complex. The crude product was diluted with acetonitrile/0.1M ammonium formate (6/4) and purified by semi-preparative HPLC. The product fraction was collected, diluted with water, passed through a C18 cartridge and eluted with ethanol, yielding 23% (not corrected for decay) 4-[(E)-2-(4-{2-[2-(2-[F-18]fluoroethoxy)ethoxy]ethoxy}phenyl)vinyl]-N-methylaniline within 30 min.

b) WO2010078370

1.5 mg precursor 2b (2-{2-[2-({5-[(E)-2-{4-[(tert-butoxycarbonyl)(methyl)amino]-phenyl}vinyl]pyridin-2-yl}oxy)ethoxy]ethoxy}ethyl 4-methylbenzenesulfonate) in 2 mL DMSO was reacted with [F-18]fluoride/kryptofix/potassium carbonate complex. The intermediate was deprotected with HCl and diluted with 1% NaOH solution for neutralization. The mixture was loaded onto a reverse phase cartridge. The cartridge was washed with water (containing 5% w/v sodium ascorbate). The crude product was eluted with acetonitrile into a reservoir containing water+5% w/v sodium ascorbate and HPLC solvent. After purification by semi-preparative HPLC, the product fraction was collected into a reservoir containing water+0.5% w/v sodium ascorbate. The solution was passed trough a C18 cartridge, the cartridge was washed with water (containing 0.5% w/v sodium ascorbate and the final product was eluted with ethanol into a vial containing 0.9% sodium chloride solution with 0.5% w/v sodium ascorbate.

c) Y. Liu et al., Nuclear Medicine and Biology 37 (2010) 917-925

1 mg precursor 2b (2-{2-[2-({5-[(E)-2-{4-[(tert-butoxycarbonyl)(methyl)amino]-phenyl}vinyl]pyridin-2-yl}oxy)ethoxy]ethoxy}ethyl 4-methylbenzenesulfonate) in 1 mL DMSO was reacted with [F-18]fluoride/kryptofix/potassium carbonate complex (synthesis using tetrabutylammonium [F-18]fluoride in acetonitrile was found to be inferior). The intermediate was deprotected with HCl and diluted with 1% NaOH solution. The mixture was loaded onto a Oasis HLB cartridge. The cartridge was washed with water, dried under a flow of argon and the product was eluted with ethanol into a vial containing a saline solution. Although, radiochemical impurities were removed by this procedure, non-radioactive by-products derived from hydrolysis of the excess of precursor, remained in the final product solution.

The yield for 4-[(E)-2-(6-{2-[2-(2-[F-18]fluoroethoxy)ethoxy]ethoxy}pyridin-3-yl)vinyl]-N-methylaniline was 34% (non-decay corrected) within 50 min at a radioactive level from 10-100 mCi (370-3700 MBq).

A "GMP compliant" manufacturing process for 4-[(E)-2-(6-{2-[2-(2-[F-18]fluoroethoxy)ethoxy]-ethoxy}pyridin-3-yl)vinyl]-N-methylaniline is disclosed in WO2010078370 and C.-H. Yao et al., Applied Radiation and Isotopes 68 (2010) 2293-2297. The radiolabeling was performed in DMSO and to prevent the decomposition of 4-[(E)-2-(6-{2-[2-(2-[F-18]fluoroethoxy)ethoxy]-ethoxy}pyridin-3-yl)vinyl]-N-methylaniline, sodium ascorbate was added to the HPLC solvent (45% acetonitrile, 55% 20 mM ammoniumacetate containing 0.5% (w/v) sodium ascorbate) and the final Formulation (0.5% (w/v) sodium ascorbate). The process afforded up to 18.5 GBq (25.4±7.7%, decay corrected) 4-[(E)-2-(6-{2-[2-(2-[F-18]fluoroethoxy)ethoxy]-ethoxy}pyridin-3-yl)vinyl]-N-methylaniline. The radiochemical purity was 95.3±2.2%.

So far, the radiolabelings of fluoropegylated (aryl/heteroaryl vinyl)-phenyl methyl amines have been performed in DMSO as solvent for the radiofluorination. It is known, that DMSO often has advantages, especially regarding solubility of lipophilic Aβ ligands compared to acetonitrile (K. Serdons et al.; Journal of Medicinal Chemistry, 52 (2009) 1428-1437).

On the other hand, DMSO is well known to decrease the resolution of RP-HPLC. In the described examples from the literature, the crude product mixture was extracted with ethyl acetate (W. Zhang et al., WO2006066104) or passed through an additional solid-phase extraction cartridge (e.g.: S. R. Choi et al., WO2010078370) to remove DMSO prior HPLC.

An other drawback of DMSO is the limited compatibility to various plastics. Therefore DMSO can not be used on all automated synthesizers. At the most commonly used "cassette-type" synthesizer Tracerlab MX (GE, former Coincidence) single-use "cassettes" made of standard molded stopcock manifolds are used. On the one hand, this concept offers a maximum of safety and reliability, since all parts directly involved in the manufacturing of the radiopharmaceutical are provided ready for use. No cleaning of the apparatus is necessary prior next synthesis. On the other hand, the cassette material is not resistant to solvents such as DMSO (R. Krasikova, Synthesis Modules and Automation in F-18 Labeling, (2006), in: Schubiger P. A., Friebe M., Lehmann L., (eds), PET-Chemistry—The Driving Force in Molecular Imaging. Springer, Berlin Heidelberg, pp. 289-316).

The use of tert-alcohols as disclosed US20100113763 has the drawback, that the solvent needs to be removed (by evaporation) prior purification by HPLC. However, the concentration/drying of the radiolabeled derivative—that is known to be sensitive towards radiolysis—includes the risk of decomposition. This limits the up-scaling of the described process.

The problem to be solved by the present invention was to provide a robust and reliable process for the manufacturing F-18 labeled fluoropegylated (aryl/heteroaryl vinyl)-phenyl derivatives, that:

provides high yield of the radiotracer allows a purification of the radiotracer from radioactive and non-radioactive by-products can be used on non-cassette type modules (such as Eckert&Ziegler Modular-Lab, GE Tracerlab FX, Raytest SynChrom)

can be used on cassette type modules (such as GE Tracerlab MX, GE Fastlab, IBA Synthera, Eckert&Ziegler Modular-Lab PharmTracer)

is compatible to plastics, valves and tubings of disposable cassettes, that are used for modules such as GE Tracerlab MX, IBA Synthera provides high yield of the radiotracer within a broad range of radioactivity not requires additional manufacturing steps such as extraction or solid-phase extraction prior HPLC purification Despite the reports from the literature, indicating that the synthesis of F-18 labeled fluoropegylated (aryl/heteroaryl vinyl)-phenyl derivatives should be performed in DMSO, processes with acetonitrile, as described in the present invention, were found to solve the problems described above. Excellent radiochemical yields, superior to the results from the literature are obtained and improved separation of the F-18 tracer from by-products is demonstrated. Additionally, the processes described herein can be used on standards non-cassette type as well as on cassette-type modules (e.g. Tracerlab MX) using standard molded stopcock manifolds.

The Process disclosed herein is more simple than processes described before, neither an liquid-liquid extraction (W. Zhang et al., WO2006066104), nor a solid-phase extraction (e.g.: S. R. Choi et al., WO2010078370), nor an evaporation is required prior purification (e.g. by HPLC). This simplified process reduces the risk for losses (during extraction or solid phase extraction) or for decomposition by radiolysis while concentration (during solid phase extraction or evaporation). Furthermore, less process steps also contribute to a shorter overall manufacturing time.

Additionally, the Method of the present invention provides the F-18 tracer with reliably high yields working in a broad range of radioactivity in contrast to processes that have been described earlier (e.g. Zhang et al., WO200606614, Choi et al., WO2010078370) wherein the up-scaling is limited, affording lower yields especially at higher levels of activity (Example 8, FIG. 9). The method of the present invention also provides results with higher yields and less deviation of results compared to the recently described method of US20100113763 (Example 9, FIG. 10).

SUMMARY OF THE INVENTION

The present invention provides a Method for production of radiolabeled compound of Formula I and suitable salts of an inorganic or organic acid thereof, hydrates, complexes, esters, amides, solvates and prodrugs thereof and optionally a pharmaceutically acceptable carrier, diluent, adjuvant or excipient.

The method comprises the steps of:
Radiofluorination of compound of Formula II
Optionally, cleavage of a protecting group
Purification and Formulation of compound of Formula I

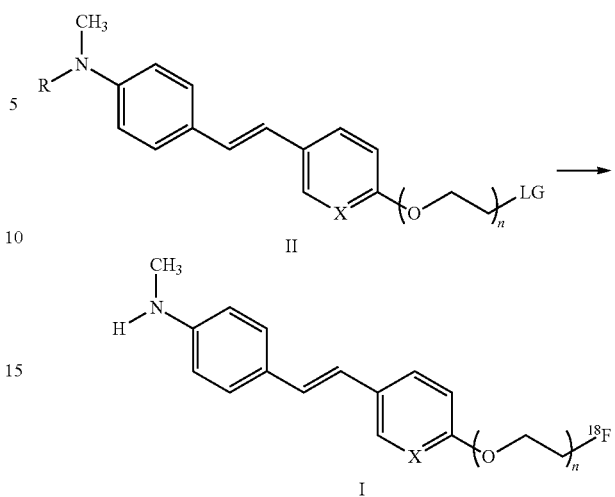

The present invention also provides compositions comprising a radiolabeled compound of Formula I or suitable salts of an inorganic or organic acid thereof, hydrates, complexes, esters, amides, solvates and prodrugs thereof and optionally a pharmaceutically acceptable carrier, diluent, adjuvant or excipient.

The present invention also provides a Kit for preparing a radiopharmaceutical preparation by the herein described process, said Kit comprising a sealed vial containing a predetermined quantity of the compound of Formula II.

DESCRIPTION OF THE INVENTION

In a first aspect the present invention is directed to a Method for producing compound of Formula I

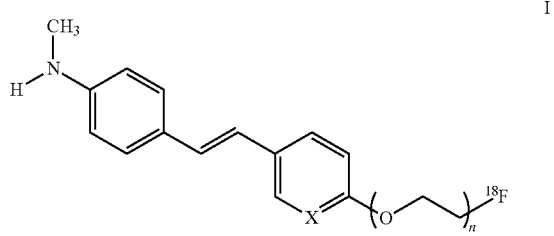

comprising the steps of:

Step 1: Radiolabeling compound of Formula II with a F-18 fluorinating agent, to obtain compound of Formula I, if R=H or to obtain compound of Formula III, if R=PG

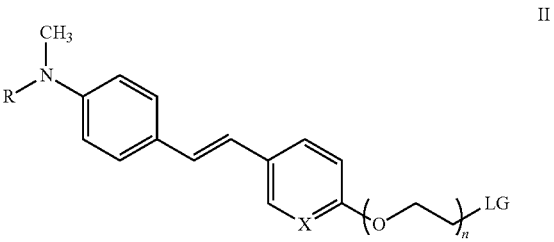

-continued

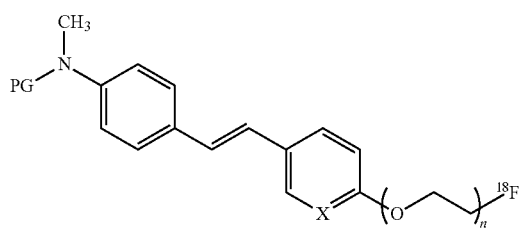

III

Step 2: Optionally, if R=PG, cleavage of the protecting group PG to obtain compound of Formula I
Step 3: Purification and Formulation of compound of Formula I
wherein:
n=1-6, preferably 2-4, more preferably 3.
X is selected from the group comprising
a) CH,
b) N.
  In one preferred embodiment, X=CH.
  In another preferred embodiment, X=N.
R is selected from the group comprising
a) H,
b) PG.
PG is an "Amine-protecting group".
  In a preferred embodiment, PG is selected from the group comprising:
a) Boc,
b) Trityl and
c) 4-Methoxytrityl.
  In a more preferred embodiment, R is H.
  In another more preferred embodiment, R is Boc.
LG is a Leaving group.
  In a preferred embodiment, LG is selected from the group comprising:
a) Halogen and
b) Sulfonyloxy.
  Halogen is chloro, bromo or iodo. Preferably, Halogen is bromo or chloro.
  In a preferred embodiment LG is contains 0-3 fluorine atoms.
  In a preferred embodiment Sulfonyloxy is selected from the group consisting of Methanesulfonyloxy. p-Toluenesulfonyloxy, Trifluormethylsulfonyloxy, 4-Cyanophenylsulfonyloxy, 4-Bromophenylsulfonyloxy, 4-Nitrophenylsulfonyloxy, 2-Nitrophenylsulfonyloxy, 4-Isopropyl-phenylsulfonyloxy, 2,4,6-Triisopropyl-phenylsulfonyloxy, 2,4,6-Trimethylphenylsulfonyloxy, 4-tert-Butyl-phenylsulfonyloxy, 4-Adamantylphenylsulfonyloxy and 4-Methoxyphenylsulfonyloxy.
  In a more preferred embodiment, Sulfonyloxy is selected from the group comprising:
a) Methanesulfonyloxy,
b) p-Toluenesulfonyloxy
c) (4-Nitrophenyl)sulfonyloxy,
d) (4-Bromophenyl)sulfonyloxy.
  In a even more preferred embodiment LG is Methanesulfonyloxy.
  In another even more preferred embodiment LG is p-Toluenesulfonyloxy.
  A preferred compound of Formula I is:

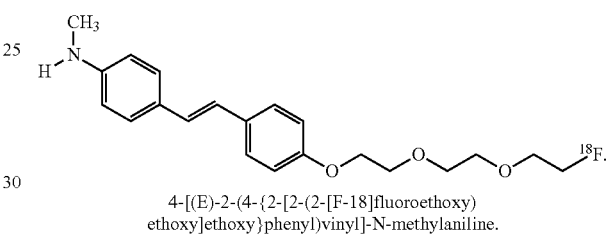

4-[(E)-2-(4-{2-[2-(2-[F-18]fluoroethoxy)ethoxy]ethoxy}phenyl)vinyl]-N-methylaniline.

Another preferred compound of Formula I is:

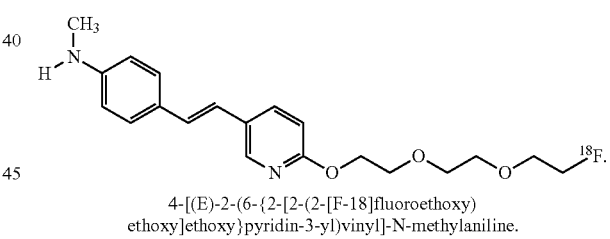

4-[(E)-2-(6-{2-[2-(2-[F-18]fluoroethoxy)ethoxy]ethoxy}pyridin-3-yl)vinyl]-N-methylaniline.

A preferred compound of Formula II is:

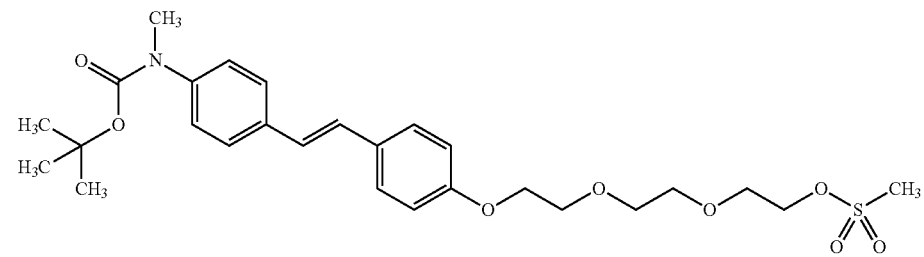

2-[2-(2-{4-[(E)-2-{4-[(tert-butoxycarbonyl)(methyl)amino]phenyl}vinyl]phenoxy}-ethoxy)ethoxy]ethyl methanesulfonate.

Another preferred compound of Formula II is:

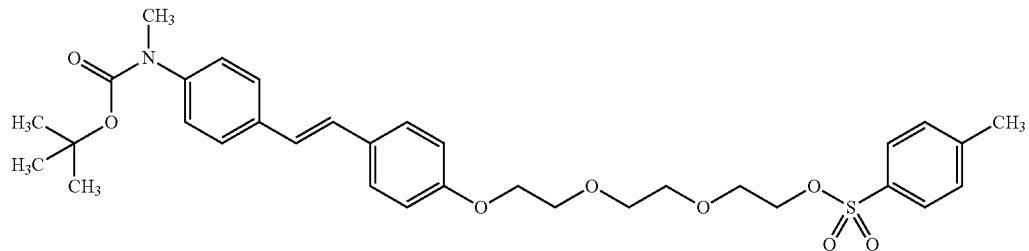

2-[2-(2-{4-[(E)-2-{4-[(tert-butoxycarbonyl)(methyl)
amino]phenyl}vinyl]phenoxy}-ethoxy)ethoxy]ethyl 4-methylbenzenesulfonate Another preferred compound of Formula II is:

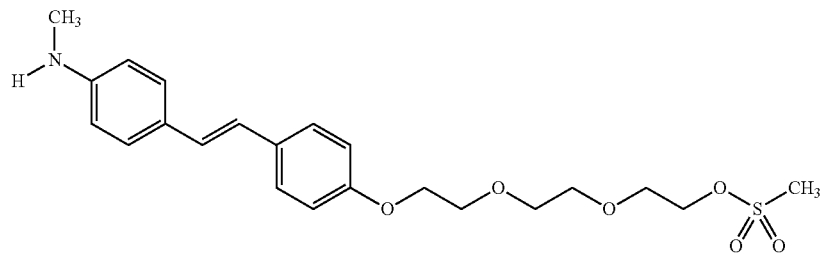

2-{2-[2-(4-{(E)-2-[4-(methylamino)phenyl]vinyl}phenoxy)ethoxy]ethoxy}ethyl 4-methylbenzenesulfonate Another preferred compound of Formula II is:

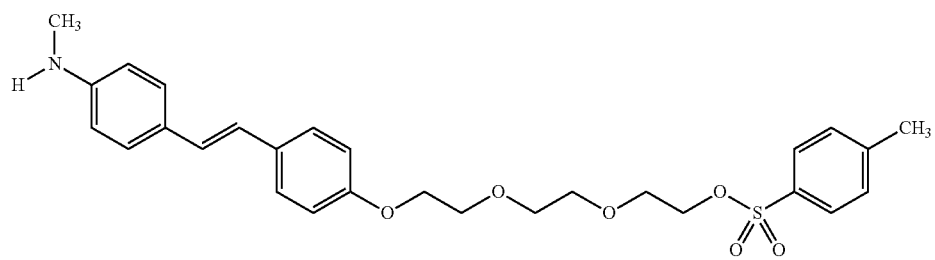

2-{2-[2-(4-{(E)-2-[4-methylamino)phenyl]vinyl}phenoxy)ethoxy]ethoxy}ethyl 4-methylbenzenesulfonate Another preferred compound of Formula II is:

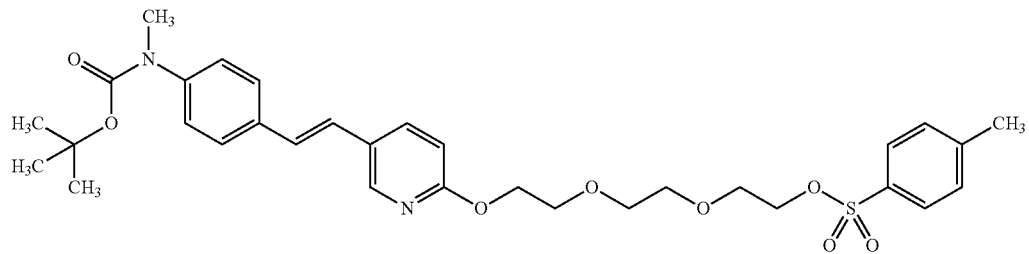

2-{2-[2-({5-[(E)-2-{4-[(tert-butoxycarbonyl)(methyl)amino]phenyl}vinyl]pyridin-2-yl}oxy)ethoxy]ethoxy}ethyl 4-methylbenzenesulfonate Step 1 comprises a straight forward [F-18]fluoro labeling reaction from compounds of Formula II for obtaining compound of Formula I (if R=H) or compound of Formula III (if R=PG).

The radiolabeling method comprises the step of reacting a compound of Formula II with a F-18 fluorinating agent for obtaining a compound of Formula III. In a preferred embodiment, the [F-18]fluoride derivative is 4,7,13,16,21,24-Hexaoxa-1,10-diazabicyclo[8.8.8]-hexacosane K[F-18]F (crownether salt of K[F-18]F), K[F-18]F, H[F-18]F, KH[F-18]F$_2$, Cs[F-18]F, Na[F-18]F or tetraalkylammonium salt of [F-18]F (e.g. [F-18]tetrabutylammonium fluoride). More preferably, the fluorination agent is K[F-18]F, H[F-18]F, [F-18]tetrabutylammonium fluoride, Cs[F-18]F or KH[F-18]F$_2$, most preferably K[F-18], Cs[F-18]F or [F-18]tetrabutylammonium fluoride.

An even more preferred F-18 fluorinating agent is kryptofix/potassium[F-18]fluoride, preferably generated from [F-18]fluoride, kryptofix and potassium carbonate.

The radiofluorination reactions are carried out in acetonitrile, or in a mixture of acetonitrile and a co-solvent which are well known to someone skilled in the art. Additionally, water and/or alcohols can be involved in such a reaction as co-solvent. The radiofluorination reactions are conducted for less than 60 minutes. Preferred reaction times are less than 30 minutes. Further preferred reaction times are less than 15 min. This and other conditions for such radiofluorination are known to experts (Coenen, Fluorine-18 Labeling Methods: Features and Possibilities of Basic Reactions, (2006), in: Schubiger P. A., Friebe M., Lehmann L., (eds), PET-Chemistry—The Driving Force in Molecular Imaging. Springer, Berlin Heidelberg, pp. 15-50).

In a preferred embodiment, the Radiofluorination of compound of Formula II is carried out in acetonitrile or in a mixture of acetonitrile and co-solvents, wherein the percentage of acetonitrile is at least 50%, more preferably v70%, even more preferably 90%.

In a preferred embodiment, the Radiofluorination of compound of Formula II is carried out in acetonitrile or in a mixture of acetonitrile and co-solvents, wherein the percentage of acetonitrile is at least 50%, more preferably at least 70%, even more preferably at least 90%.

Preferably, the radiolabeling is performed with a solution of compound of Formula II in acetonitrile or an acetonitrile/co-solvent mixture, wherein the volume of that solution is 100 µL-5000 µL, preferably 250 µL-3000 µL, more preferably 500 µL-2000 µL.

In one embodiment, 7.5-75 µmol, preferably 10-50 µmol, more preferably 10-30 µmol and even more preferably 12-25 µmol and even more preferably 13-25 µmol of compound of Formula II are used in Step 1.

In another embodiment, more than 7.5 µmol, preferably more than 10 µmol, and more preferable more than 12 µmol and even more preferably more than 13 µmol of compound of Formula II are used in Step 1.

In another embodiment, more than 5 mg, preferably more than 6 mg and more preferably more than 7 mg of compound of Formula II are used in Step 1.

In another embodiment 7 mg of compound of Formula II are used in Step 1.

In another embodiment 8 mg of compound of Formula II are used in Step 1.

In an other embodiment, 1.5-50 µmol/mL, preferably 5-25 µmol/mL, more preferably 7-20 µmol/mol of a solution of compound of Formula II in acetonitrile or an acetonitrile/co-solvent mixture is used in Step 1.

Optionally, if R=PG, Step 2 comprises the deprotection of compound of Formula III to obtain compound of Formula I. Reaction conditions are known or obvious to someone skilled in the art, which are chosen from but not limited to those described in the textbook Greene and Wuts, Protecting groups in Organic Synthesis, third edition, page 494-653, included herewith by reference.

Preferred reaction conditions are addition of an acid and stirring at 0° C.-180° C.; addition of an base and heating at 0° C.-180° C.; or a combination thereof.

Preferably the Step 1 and Step 2 are performed in the same reaction vessel.

Step 3 comprises the purification and formulation of compound of Formula I. Methods for purification of radiotracers are well known to person skilled in the art and include HPLC methods as well as solid-phase extraction methods.

In one embodiment, the crude product mixture is purified by HPLC and the collected product fraction is further passed through a solid-phase cartridge to remove the HPLC solvent (such as acetonitrile) and to provide the compound of Formula I in an injectable Formulation.

In an other embodiment, the crude product mixture is purified by HPLC, wherein, the HPLC solvent mixture (e.g. mixtures of ethanol and aqueous buffers) can be part of the injectable Formulation of compound of Formula I. The collected product fraction can be diluted or mixed with other parts of the Formulation.

In an other embodiment, the crude product mixture is purified by solid-phase cartridges.

In a preferred embodiment, the Method for manufacturing of compound of Formula I is carried out by use of a module (review: Krasikowa, Synthesis Modules and Automation in F-18 labeling (2006), in: Schubiger P. A., Friebe M., Lehmann L., (eds), PET-Chemistry—The Driving Force in Molecular Imaging. Springer, Berlin Heidelberg, pp. 289-316) which allows an automated synthesis. More preferably, the Method is carried out by use of an one-pot module. Even more preferable, the Method is carried out on commonly known non-cassette type modules (e.g. Eckert&Ziegler Modular-Lab, GE Tracerlab FX, Raytest SynChrom) and cassette type modules (e.g. GE Tracerlab MX, GE Fastlab, IBA Synthera, Eckert&Ziegler Modular-Lab PharmTracer), optionally, further equipment such as HPLC or dispensing devices are attached to the said modules.

In a second aspect the present invention is directed to a fully automated and/or remote controlled Method for production of compound of Formula I wherein compounds of Formula I, II and III and Steps 1, 2 and 3 are described above.

In a preferred embodiment this method is a fully automated process, compliant with GMP guidelines, that provides a Formulation of Formula I for the use of administration (injection) into human.

In a third aspect the present invention is directed to a Kit for the production of a pharmaceutical composition of compound of Formula I.

In one embodiment the Kit comprising a sealed vial containing a predetermined quantity of the compound of Formula II and acetonitrile or acetonitrile and a co-solvent for dissolving compound of Formula II.

In a preferred embodiment, compound of Formula II is dissolved in acetonitrile or in a mixture of acetonitrile and co-solvents, wherein the percentage of acetonitrile is at least 50%, more preferably 70%, even more preferably 90%.

Preferably, the Kit contains 1.5-75 µmol, preferably 7.5-50 µmol, more preferably 10-30 µmol and even more preferably 12-25 µmol and even more preferably 13-25 µmol of compound of Formula II.

In another embodiment the Kit contains more than 7.5 µmol, preferably more than 10 µmol and more preferably more than 12 µmol and even more preferably more than 13 µmol of compound of Formula II.

In another embodiment the Kit contains more than 5 mg, preferably more than 6 mg and more preferably more than 7 mg of compound of Formula II.

In another embodiment the Kit contains 7 mg of compound of Formula II.

In another embodiment the Kit contains 8 mg of compound of Formula II.

Optionally, the Kit provides compound of Formula II in solution of acetonitrile or acetonitrile and a co-solvent. In a preferred embodiment, compound of Formula II is dissolved in acetonitrile or in a mixture of acetonitrile and co-solvents, wherein the percentage of acetonitrile is at least 50%, more preferably 70%, even more preferably 90%.

Optionally, the Kit provides compound of Formula II in solution of acetonitrile or acetonitrile and a co-solvent. In a preferred embodiment, compound of Formula II is dissolved in acetonitrile or in a mixture of acetonitrile and co-solvents, wherein the percentage of acetonitrile is at least 50%, more preferably at least 70%, even more preferably at least 90%.

Optionally, the Kit contains further components for manufacturing of compound of Formula I, such as solid-phase extraction cartridges, reagent for fluorination (as described above), reagent for cleavage of deprotection group, solvent or solvent mixtures for purification, solvents and excipient for formulation.

In one embodiment, the Kit contains a platform (e.g. cassette) for a "cassette-type module" (such as Tracerlab MX or IBA Synthera).

DEFINITIONS

In the context of the present invention, preferred salts are pharmaceutically suitable salts of the compounds according to the invention. The invention also comprises salts which for their part are not suitable for pharmaceutical applications, but which can be used, for example, for isolating or purifying the compounds according to the invention.

Pharmaceutically suitable salts of the compounds according to the invention include acid addition salts of mineral acids, carboxylic acids and sulphonic acids, for example salts of hydrochloric acid, hydrobromic acid, sulphuric acid, phosphoric acid, methanesulphonic acid, ethanesulphonic acid, toluenesulphonic acid, benzenesulphonic acid, naphthalene disulphonic acid, acetic acid, trifluoroacetic acid, propionic acid, lactic acid, tartaric acid, malic acid, citric acid, fumaric acid, maleic acid and benzoic acid.

Pharmaceutically suitable salts of the compounds according to the invention also include salts of customary bases, such as, by way of example and by way of preference, alkali metal salts (for example sodium salts and potassium salts), alkaline earth metal salts (for example calcium salts and magnesium salts) and ammonium salts, derived from ammonia or organic amines having 1 to 16 carbon atoms, such as, by way of example and by way of preference, ethylamine, diethylamine, triethylamine, ethyldiisopropylamine, monoethanolamine, diethanolamine, triethanolamine, dicyclohexylamine, dimethylaminoethanol, procaine, dibenzylamine, N methylmorpholine, arginine, lysine, ethylenediamine and N methylpiperidine.

The term Halogen or halo refers to Cl, Br, F or I.

The term "Amine-protecting group" as employed herein by itself or as part of another group is known or obvious to someone skilled in the art, which is chosen from but not limited to a class of protecting groups namely carbamates, amides, imides, N-alkyl amines, N-aryl amines, imines, enamines, boranes, N—P protecting groups, N-sulfenyl, N-sulfonyl and N-silyl, and which is chosen from but not limited to those described in the textbook Greene and Wuts, Protecting groups in Organic Synthesis, third edition, page 494-653, included herewith by reference. The amine-protecting group is preferably Carbobenzyloxy (Cbz), p-Methoxybenzyl carbonyl (Moz or MeOZ), tert-Butyloxycarbonyl (BOC), 9-Fluorenylmethyloxycarbonyl (FMOC), Benzyl (Bn), p-Methoxybenzyl (PMB), 3,4-Dimethoxybenzyl (DMPM), p-methoxyphenyl (PMP) or the protected amino group is a 1,3-dioxo-1,3-dihydro-2H-isoindol-2-yl (phthalimido) or an azido group.

The term "Leaving group" as employed herein by itself or as part of another group is known or obvious to someone skilled in the art, and means that an atom or group of atoms is detachable from a chemical substance by a nucleophilic agent. Examples are given e.g. in Synthesis (1982), p. 85-125, table 2 (p. 86; (the last entry of this table 2 needs to be corrected: "n-$C_4F_9S(O)_2$—O— nonaflat" instead of "n-$C_4H_9S(O)_2$—O— nonaflat"), Carey and Sundberg, Organische Synthese, (1995), page 279-281, table 5.8; or Netscher, Recent Res. Dev. Org. Chem., 2003, 7, 71-83, scheme 1, 2, 10 and 15 and others). (Coenen, Fluorine-18 Labeling Methods: Features and Possibilities of Basic Reactions, (2006), in: Schubiger P. A., Friebe M., Lehmann L., (eds), PET-Chemistry—The Driving Force in Molecular Imaging. Springer, Berlin Heidelberg, pp. 15-50, explicitly: scheme 4 pp. 25, scheme 5 pp 28, table 4 pp 30, Fig 7 pp 33).

The term Sulfonyloxy refers to —O—$S(O)_2$-Q wherein Q is optionally substituted aryl or optionally substituted alkyl.

The term "alkyl" as employed herein by itself or as part of another group refers to a $C_1$-$C_{10}$ straight chain or branched alkyl group such as, for example methyl, ethyl, propyl, isopropyl, butyl, isobutyl, tert-butyl, pentyl, isopentyl, neopentyl, heptyl, hexyl, decyl or adamantyl. Preferably, alkyl is $C_1$-$C_6$ straight chain or branched alkyl or $C_7$-$C_{10}$ straight chain or branched alkyl. Lower alkyl is a $C_1$-$C_6$ straight chain or branched alkyl.

The term "aryl" as employed herein by itself or as part of another group refers to monocyclic or bicyclic aromatic groups containing from 6 to 10 carbons in the ring portion, such as phenyl, naphthyl or tetrahydronaphthyl.

Whenever the term "substituted" is used, it is meant to indicate that one or more hydrogens on the atom indicated in the expression using "substituted" is/are replaced by one ore multiple moieties from the group comprising halogen, nitro, cyano, trifluoromethyl, alkyl and O-alkyl, provided that the regular valency of the respective atom is not exceeded, and that the substitution results in a chemically stable compound, i.e. a compound that is sufficiently robust to survive isolation to a useful degree of purity from a reaction mixture.

Unless otherwise specified, when referring to the compounds of Formula the present invention per se as well as to any pharmaceutical composition thereof the present invention includes all of the hydrates, salts, and complexes.

The term "F-18" means fluorine isotope $^{18}F$. The term "F-19" means fluorine isotope $^{19}F$.

EXAMPLES

Determination of Radiochemical and Chemical Purity

Radiochemical and chemical purities of 4-[(E)-2-(4-{2-[2-(2-[F-18]fluoroethoxy)ethoxy]-ethoxy}phenyl)vinyl]-N- methylaniline and 4-[(E)-2-(4-{2-[2-(2-[F-18]fluoroethoxy)ethoxy]-ethoxy}phenyl)vinyl]-N-methylaniline were determined by analytical HPLC (column: Atlantis T3; 150× 4.6 mm, 3 μm, Waters; solvent A: 5 mM $K_2HPO_4$ pH 2.2; solvent B: acetonitrile; flow: 2 mL/min, gradient: 0:00 min 40% B, 0:00-05:50 min 40-90% B, 05:50-05:60 min 90-40% B, 05:60-09:00 min 40% B).

Retention time of 4-[(E)-2-(4-{2-[2-(2-[F-18]fluoroethoxy)ethoxy]-ethoxy}phenyl)-vinyl]-N-methylaniline: 3.50-3.95 min depending, on the HPLC system used for quality control. Due to different equipment (e.g tubing) a difference in retention time is observed between the different HPLC systems. The identity of 4-[(E)-2-(4-{2-[2-(2-[F-18]fluoroethoxy)ethoxy]-ethoxy}phenyl)vinyl]-N-methylaniline was proofed by co-injection with the non-radioactive reference 4-[(E)-2-(4-{2-[2-(2-[F-19]fluoroethoxy)ethoxy]-ethoxy}phenyl)vinyl]-N-methylaniline.

Retention time of 4-[(E)-2-(6-{2-[2-(2-[F-18]fluoroethoxy)ethoxy]-ethoxy}pyridin-3-yl)vinyl]-N-methylaniline: 3.47 min. The identity of 4-[(E)-2-(6-{2-[2-(2-[F-18]fluoroethoxy)ethoxy]-ethoxy}pyridin-3-yl)vinyl]-N-methylaniline was proofed by co-elution with the non-radioactive reference -[(E)-2-(6-{2-[2-(2-[F-19]fluoroethoxy)ethoxy]-ethoxy}pyridin-3-yl)vinyl]-N-methylaniline.

Example 1

Comparison of 4-[(E)-2-(4-{2-[2-(2-[F-18]fluoroethoxy)ethoxy]-ethoxy}phenyl)vinyl]-N-methylaniline Radiosynthesis on GE Tracerlab $FX_N$ Using Acetonitrile vs. DMSO as Solvent for Radiofluorination

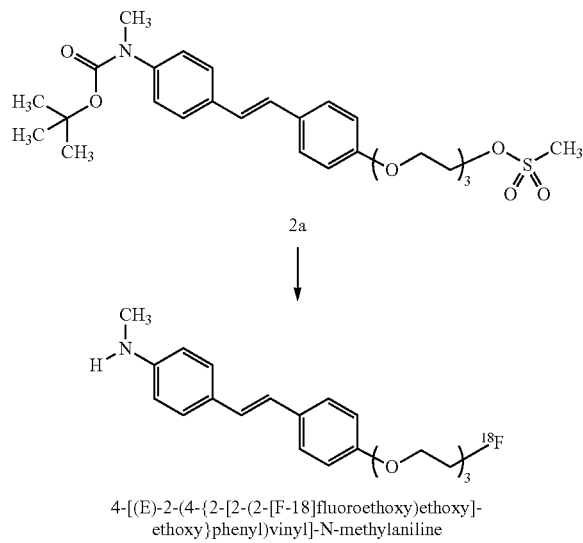

4-[(E)-2-(4-{2-[2-(2-[F-18]fluoroethoxy)ethoxy]-ethoxy}phenyl)vinyl]-N-methylaniline The synthesis of 4-[(E)-2-(4-{2-[2-(2-fluoroethoxy)ethoxy]-ethoxy}phenyl)vinyl]-N-methylaniline have been performed on a Tracerlab $FX_N$ synthesizer (FIG. 1) using acetonitrile or DMSO as solvent for fluorination. The setup of the synthesizer and the results are summarized in Table 1.

[F-18]Fluoride was trapped on a QMA cartridge (C1, FIG. 1). The activity was eluted with potassium carbonate/kryptofix mixture (from "V1") into the reactor. The solvent was removed while heating under gentle nitrogen stream and vacuum. Drying was repeated after addition of acetonitrile (from "V2"). The solution of 2a (from "V3") was added to the dried residue and the mixture was heated for 8 min at 120° C. After cooling to 60° C., HCl/acetonitrile mixture (from "V4") was added and solution was heated for 4 min at 110° C.

To remove DMSO prior semi-preparative HPLC, the crude product of the DMSO labeling was diluted with water from the "Mix-Vial" and was subsequently passed trough a C18 light cartridge (C2, FIG. 1). The cartridge was washed with water from "V5" into the "Mix-Vial" and subsequently removed into the waste bottle through the injection valve. The crude product was eluted with acetonitrile from "V6" into the "Mix-Vial" and diluted with ammonium formate solution from "V7". The mixture was purified by semi-preparative HPLC. The product fraction was collected into the "Flask" containing 30 mL water. the solution was passed through a tC18 plus cartridge (C3). The cartridge was washed with 20% ethanol in water from "V9" and 4-[(E)-2-(4-{2-[2-(2-fluoroethoxy)ethoxy]-ethoxy}phenyl)vinyl]-N-methylaniline was eluted with 1.5 mL ethanol into the product vial containing 8.5 mL formulation basis (consisting of phosphate buffer, PEG400 and ascorbic acid).

In contrast, it was found, that no C18 cartridge (C2, FIG. 1) is needed if acetonitrile is used as solvent for fluorination. No solvents/reagents were filled into "V5" and "V7". The crude product mixture was diluted with 1 mL 1M NaOH and 2 mL ammonium formate (0.1M) from "V6" and then directly transferred to the HPLC via ("Mix-Vial").

A higher radiochemical yield of 50% (not corrected for decay) was obtained using 7 mg 2a in 1 mL acetonitrile compared to the process using 7 mg 2a in 1 mL DMSO that afforded 38% (not corrected for decay) 4-[(E)-2-(4-{2-[2-(2-[F-18]fluoroethoxy)ethoxy]-ethoxy}phenyl)vinyl]-N-methylaniline.

TABLE 1

Setup of Tracerlab $FX_N$ for synthesis of 4-[(E)-2-(4-{2-[2-(2-[F-18]fluoroethoxy)ethoxy]-ethoxy}phenyl)vinyl]-N-methylaniline

|  | Radiolabeling in DMSO | Radiolabeling in acetonitrile |
|---|---|---|
| Vial V1 | 1.5 mg potassium carbonate, 5 mg kryptofix in 0.075 mL water and 1.425 mL acetonitrile | |
| Vial V2 | 1 mL acetonitrile for drying | |
| Vial V3 | 7 mg precursor 2a in 1 mL DMSO | 7 mg precursor 2a in 1 mL acetonitrile |
| Vial V4 | 0.5 mL 2M HCl and 0.5 mL acetonitrile | |
| Vial V5 | 5 mL water | — |
| Vial V6 | 3 mL acetonitrile | 1 mL 1M NaOH and 2 mL ammonium formate (0.1M) |
| Vial V7 | 2 mL ammonium formate (0.1M) | — |
| Vial V8 | 1.5 mL ethanol | |
| Vial V9 | 5 mL (20% ethanol in water) | |
| Cartridge C1 | QMA light (Waters) | |
| Cartridge C2 | C18 light (Waters) | — |
| Cartridge C3 | tC18 plus (Waters) | |
| Mix-Vial | 7 mL water | — |
| Flask | 30 mL water | |
| HPLC column | Zorbax Bonus RP, 9.4 * 250 mm; 5 μm; (Agilent) | |
| HPLC solvent | 55% acetonitrile, 45% ammonium formate (0.1M) | |
| HPLC flow | 4 mL/min | |
| Start activity of [F-18]fluoride | 2300 MBq | 3800 MBq |
| Product activity | 870 MBq | 1900 MBq |
| Radiochemical yield | 38% (not corrected for decay) | 50% (not corrected for decay) |

An additional advantage of the process wherein acetonitrile is used instead of DMSO is pattern of the semi-preparative HPLC. Despite the an additional C18 cartridge, residual DMSO lead to broad product peak (FIG. 2) whereas the process using acetonitrile lead to a sharp peak with improved separation from non-radioactive by-products on the same semi-preparative HPLC column (FIG. 3).

Example 2

Comparison of 4-[(E)-2-(6-{2-[2-(2-[F-18]fluoroethoxy)ethoxy]-ethoxy}pyridin-3-yl)vinyl]-N-methylaniline Synthesis on GE Tracerlab $FX_N$ Using Acetonitrile vs. DMSO as Solvent for Radiofluorination

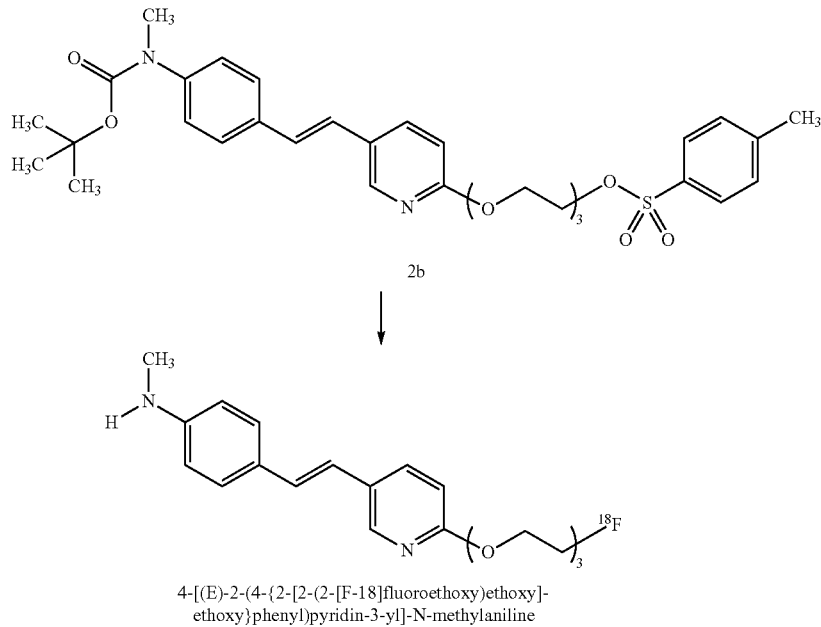

4-[(E)-2-(4-{2-[2-(2-[F-18]fluoroethoxy)ethoxy]-ethoxy}phenyl)pyridin-3-yl]-N-methylaniline The synthesis of 4-[(E)-2-(6-{2-[2-(2-[F-18]fluoroethoxy)ethoxy]-ethoxy}pyridin-3-yl)vinyl]-N-methylaniline has been performed on a Tracerlab $FX_N$ synthesizer (FIG. 1) using acetonitrile or DMSO as solvent for fluorination. The setup of the synthesizer and the results are summarized in Table 2.

[F-18]Fluoride was trapped on a QMA cartridge (C1, FIG. 1). The activity was eluted with potassium carbonate/kryptofix mixture (from "V1") into the reactor.

The solvent was removed while heating under gentle nitrogen stream and vacuum. Drying was repeated after addition of acetonitrile (from "V2"). The solution of 2b (from "V3") was added to the dried residue and the mixture was heated for 8 min at 120° C. After cooling to 60° C., HCl/acetonitrile mixture (from "V4") was added and solution was heated for 4 min at 110° C.

To remove DMSO prior semi-preparative HPLC, the crude product of the DMSO labeling was diluted with water from the "Mix-Vial" and was subsequently passed is trough a C18 light cartridge (C2, FIG. 1). The cartridge was washed with water from "V5" into the "Mix-Vial" and subsequently removed into the waste bottle through the injection valve. The crude product was eluted with acetonitrile from "V6" into the "Mix-Vial" and diluted with ammonium formate solution from "V7". The mixture was purified by semi-preparative HPLC. The product fraction was collected into the "Flask" containing 30 mL water. the solution was passed through a tC18 plus cartridge (C3). The cartridge was washed with 20% ethanol in water from "V9" and 4-[(E)-2-(4-{2-[2-(2-[F-18]fluoroethoxy)ethoxy]-ethoxy}phenyl)vinyl]-N-methylaniline was eluted with 1.5 mL ethanol into the product vial containing 8.5 mL formulation basis (consisting of phosphate buffer, PEG400 and ascorbic acid).

In contrast, it was found, that no C18 cartridge (C2, FIG. 1) is needed if acetonitrile is used as solvent for fluorination. No solvents/reagents were filled into "V5" and "V7". The crude product mixture was diluted with 1 mL 1M NaOH and 2 mL ammonium formate (0.1M) from "V6" and then directly transferred to the HPLC via ("Mix-Vial").

A higher radiochemical yield of 44% (not corrected for decay) was obtained using 7 mg 2b in 1 mL acetonitrile compared to the process using 7 mg 2b in 1 mL DMSO that afforded 34% (not corrected for decay) 4-[(E)-2-(6-{2-[2-(2-[F-18]fluoroethoxy)ethoxy]-ethoxy}pyridin-3-yl)vinyl]-N-methylaniline.

TABLE 2

Setup of Tracerlab $FX_N$ for synthesis of 4-[(E)-2-(6-{2-[2-(2-[F-18]fluoroethoxy)ethoxy]-ethoxy}pyridin-3-yl)vinyl]-N-methylaniline

|  | Radiolabeling in DMSO | Radiolabeling in acetonitrile |
| --- | --- | --- |
| Vial V1 | Potassium carbonate/kryptofix mixture | |
| Vial V2 | 1 mL acetonitrile for drying | |
| Vial V3 | 8 mg precursor 2b in 1 mL DMSO | 8 mg precursor 2b in 1 mL acetonitrile |
| Vial V4 | 0.5 mL 2M HCl and 0.5 mL acetonitrile | |
| Vial V5 | 5 mL water | v |
| Vial V6 | 3 mL acetonitrile | 1 mL 1M NaOH and 2 mL ammonium formate (0.1M) |
| Vial V7 | 2 mL ammonium formate (0.1M) | — |
| Vial V8 | 1.5 mL ethanol | |
| Vial V9 | 5 mL (20% ethanol in water) | |
| Cartridge C1 | QMA light (Waters) | |
| Cartridge C2 | C18 light (Waters) | — |
| Cartridge C3 | tC18 plus (Waters) | |
| Mix-Vial | 7 mL water | — |
| Flask | 30 mL water | |
| HPLC column | Zorbax Bonus RP, 9.4 * 250 mm; 5 μm; (Agilent) | |

TABLE 2-continued

Setup of Tracerlab $FX_N$ for synthesis of 4-[(E)-2-(6-{2-[2-(2-[F-18]fluoroethoxy)ethoxy]-ethoxy}pyridin-3-yl)vinyl]-N-methylaniline

| | Radiolabeling in DMSO | Radiolabeling in acetonitrile |
|---|---|---|
| HPLC solvent | 55% acetonitrile, 45% ammonium formate (0.1M) | |
| Start activity of [F-18]fluoride | 1800 MBq | 3700 MBq |
| Product activity | 610 MBq | 1600 MBq |
| Radiochemical yield | 34% (not corrected for decay) | 44% (not corrected for decay) |

Additionally, of the process wherein acetonitrile is used instead of DMSO is pattern of the semi-preparative HPLC. Despite the an additional C18 cartridge, residual DMSO lead to broad product peak (FIG. 4) whereas the process using acetonitrile lead to a sharp peak with improved separation from non-radioactive by-products on the same semi-preparative HPLC column (FIG. 5).

Example 3

Synthesis and purification of 4-[(E)-2-(4-{2-[2-(2-[F-18]fluoroethoxy)ethoxy]-ethoxy}phenyl)vinyl]-N-methylaniline on GE Tracerlab MX

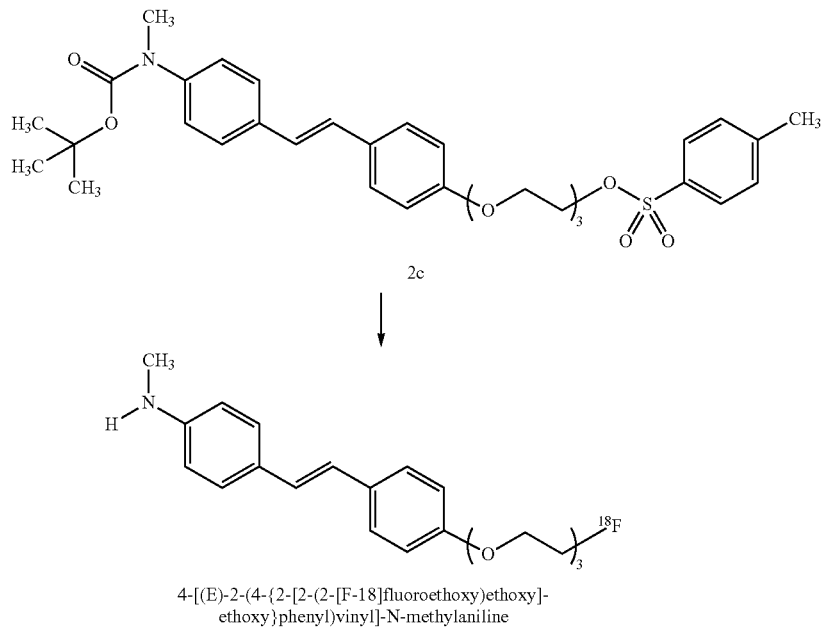

4-[(E)-2-(4-{2-[2-(2-[F-18]fluoroethoxy)ethoxy]-ethoxy}phenyl)vinyl]-N-methylaniline For synthesis and purification of 4-[(E)-2-(4-{2-[2-(2-[F-18]fluoroethoxy)ethoxy]-ethoxy}phenyl)vinyl]-N-methylaniline on the Tracerlab MX, a Kit was assembled (Table 3).

TABLE 3

Composition of Kit for manufacturing of 4-[(E)-2-(4-{2-[2-(2-[F-18]fluoroethoxy)ethoxy]-ethoxy}phenyl)vinyl]-N-methylaniline on tracerlab MX

| | |
|---|---|
| Eluent vial | 22 mg kryptofix. 7 mg potassium carbonate in 300 μL water + 300 μL acetonitrile |
| Blue capped vial | 8 mL acetonitrile |
| Red capped vial | 8 mg precursor 2c |
| Green capped vial | 2 mL 1.5M HCl |
| 2 mL syringe | 1.5 mL 2M NaOH + 0.3 mL phosphate buffer |

TABLE 3-continued

Composition of Kit for manufacturing of 4-[(E)-2-(4-{2-[2-(2-[F-18]fluoroethoxy)ethoxy]-ethoxy}phenyl)vinyl]-N-methylaniline on tracerlab MX

| | |
|---|---|
| Solvent bag 1 | 40% EtOH in phosphate buffer (pH 7.4) |
| Solvent bag 2 | 50% EtOH in phosphate buffer (pH 7.4) |
| Anion exchange cartridge | QMA light, Waters (pre-conditioned) |
| Purification cartridge | Chromabond Flash RS 4 Nucleodur 100-30 C18ec, Macherey-Nagel |
| Product vial | 50 mL vial |
| Formulation basis 1 | 100 mg Ascorbic acid |
| Formulation basis 2 | 122 mg $Na_2HPO_4 \cdot H_2O$, 8.9 mL PEG 400, 26.1 mL water |

The setup of the cassette on the MX module is illustrated in FIG. 6.

Precursor 2c was dissolved in the "red capped vial" during the synthesis sequence using approximately 1.8 mL acetonitrile from the "blue capped vial". Fluoride (2.4 GBq) was transferred to the MX module and trapped on the QMA cartridge. The activity was eluted into the reactor with potassium carbonate/kryptofix mixture from the "eluent vial". After azeotropic drying (heating, vacuum, nitrogen stream and addition of acetonitrile from the "blue capped vial"), the solution of 2c in acetonitrile was transferred from the "red capped vial" into the reactor. The resulting mixture was heated for 10 min at 120° C. HCl was transferred via the syringes from the "green capped vial" into the reactor. The mixture was heated for 5 min at 110° C. During deprotection, solvent mixture 1 from "Solvent bag 1" was flushed through the "Purification cartridge" by the left syringe. The crude product mixture was mixed with sodium hydroxid/buffer mixture from the "2 mL syringe" and diluted with the solvent 1 from "Solvent bag 1". The diluted crude product mixture was passed through "Purification cartridge". The remove non-radioactive by-products, solvent 1 from "Solvent bag 1" was filled into the left syringe and flushed through the "Purification cartridge" into the waste bottle. This procedure was repeated six times. Solvent 2 from "Solvent bag 2" was filled into the right syringe and transferred to the left syringe. Solvent 2 was flushed by the left syringe through the "Purification cartridge". The first fraction was allowed to go to the waste bottle, but a fraction of 7.5 mL was automatically collected into the right syringe. Finally, the product fraction was transferred to the product vial (that was pre-filled with Formulation basis 1 and Formulation basis 2). 770 MBq (32% not corrected for decay) 4-[(E)-2-(4-{2-[2-(2-[F-18]fluoroethoxy)ethoxy]-ethoxy}phenyl)vinyl]-N-methylaniline were obtained in 58 min overall manufacturing time. The cartridge based purification provided radiochemical and chemical pure product, similar to the purity obtained by semi-preparative HPLC (FIG. 7, FIG. 8).

Example 4

Radiolabeling of 2-[2-(2-{4-[(E)-2-{4-(methyl)amino]-phenyl}vinyl]phenoxy}ethoxy)ethoxy]ethyl 4-methylbenzenesulfonate

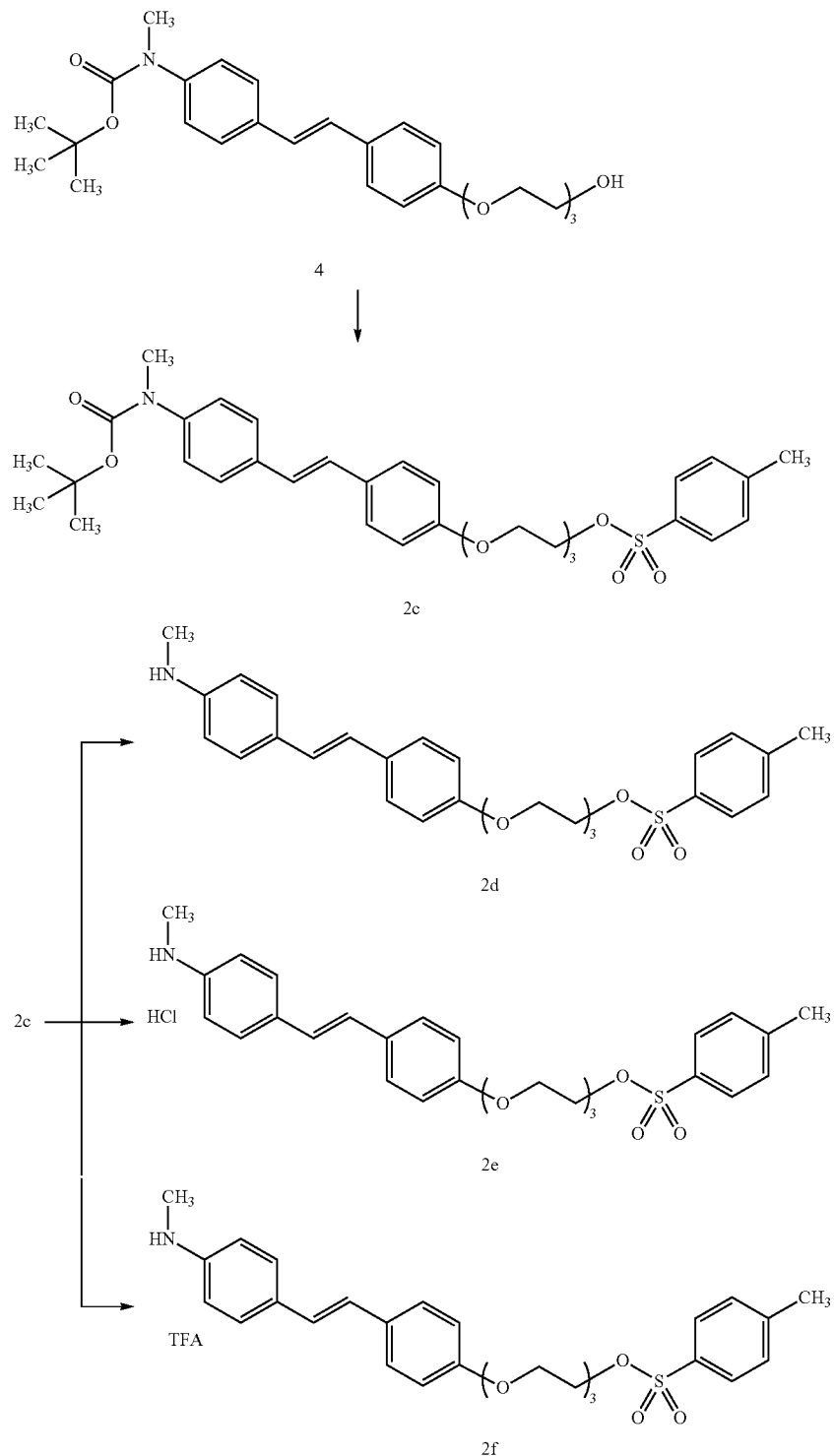

Synthesis of 2-[2-(2-{4-[(E)-2-{4-[(tert-butoxycarbonyl)(methyl)amino]phenyl}-vinyl]phenoxy}ethoxy)ethoxy]ethyl 4-methylbenzenesulfonate (2c)

4-Dimethylaminopyridine (26.7 mg) and triethylamine (225 µL) were added to a solution of 1.0 g tert-butyl {4-[(E)-2-(4-{2-[2-(2-hydroxyethoxy)ethoxy]ethoxy}phenyl)vinyl]phenyl}methylcarbamate (4) in dichloromethane (12 mL) at 0° C. A solution of p-toluenesulfonyl chloride (417 mg) in dichloromethane (13.5 mL) was added at 0° C. The resulting mixture was stirred at room temperature over night. The solvent was removed under reduced pressure and the crude product was purified by flash chromatography (silica, 0-80% ethyl acetate in hexane). 850 mg 2c were obtained as colorless solid.

$^1$H NMR (300 MHz, CDCl3) δ ppm 1.46 (s, 9H), 2.43 (s, 3H), 3.27 (s, 3H), 3.59-3.73 (m, 6H), 3.80-3.86 (m, 2H), 4.05-4.19 (m, 2H), 6.88-7.05 (m, 4H), 7.21 (d, J=8.3 Hz, 2H), 7.32 (d, J=8.3 Hz, 2H), 7.39-7-47 (m, 4H), 7.80 (d, J=8.3 Hz, 2H).

MS (ESIpos): m/z=612 (M+H)$^+$

Synthesis of 2-{2-[2-(4-{(E)-2-[4-(methylamino)phenyl]vinyl}phenoxy)ethoxy]-ethoxy}ethyl 4-methylbenzenesulfonates a) 2-{2-[2-(4-{(E)-2-[4-(methylamino)phenyl]vinyl}phenoxy)ethoxy]-ethoxy}ethyl 4-methylbenzenesulfonate (2d)

200 mg 2-[2-(2-{4-[(E)-2-{4-[(tert-butoxycarbonyl)(methyl)amino]phenyl}-vinyl]phenoxy}ethoxy)ethoxy]ethyl 4-methylbenzenesulfonate (2c) were dissolved in 2.5 mL dichloromethane. 250 µL trifluoroacetic acid were added and the mixture was stirred for 4 h at room temperature. The solvent was removed under reduced pressure. The crude product was dissolved in dichlormethane (5 mL) and washed with sodium carbonate solution (10%, 2×2 mL). The organic layer was dried over sodium sulfate, the solvent was removed under reduced pressure and the residue was purified by flash chromatography (silica, 12-100% ethyl acetate in hexane). 84 mg 2d were obtained as light red solid.

$^1$H NMR (300 MHz, CDCl$_3$) δ ppm 2.42 (s, 3H), 2.87 (s, 3H), 3.61-3.64 (m, 2H), 3.65-3.68 (m, 2H), 3.69-3.72 (m, 2H), 3.81-3.84 (m, 2H), 4.10-4.13 (m, 2H), 4.15-4.17 (m, 2H), 6.63 (d, J=8.3 Hz, 2H), 6.84-6.91 (m, 4H), 7.32 (d, J=7.9 Hz, 2H), 7.34 (d, J=8.7 Hz, 2H), 7.39 (d, J=8.7 Hz, 2H), 7.80 (d, J=8.3 Hz, 2H).

MS (ESIpos): m/z=512 (M+H)$^+$ b) 2-{2-[2-(4-{(E)-2-[4-(methylamino)phenyl]vinyl}phenoxy)ethoxy]-ethoxy}ethyl 4-methylbenzenesulfonate hydrochloride (2e)

200 mg 2-[2-(2-{4-[(E)-2-{4-[(tert-butoxycarbonyl)(methyl)amino]phenyl}-vinyl]phenoxy}ethoxy)ethoxy]ethyl 4-methylbenzenesulfonate (2c) were dissolved in a 2M solution of HCl in diethyl ether. The mixture was stirred at room temperature for 72 h. The solvent was removed under reduced pressure. Diethyl ether was added and the precipitate was collected, washed with diethyl ether and dried under reduced pressure. 160 mg 2e were obtained as light yellow solid.

$^1$H NMR (300 MHz, CDCl$_3$) δ ppm 2.43 (s, 3H), 3.03 (s, 3H), 3.62-3.64 (m, 2H), 3.66-3.68 (m, 2H), 3.69-3.72 (m, 2H), 3.82-3.85 (m, 2H), 4.12-4.14 (m, 2H), 4.16-4.18 (m, 2H), 6.88-6.94 (m, 3H), 7.04 (d, J=16.2 Hz, 1H), 7.32 (d, J=7.9 Hz, 2H), 7.42 (d, J=8.7 Hz, 2H), 7.49-7-56 (m, 4H), 7.80 (d, J=8.3 Hz, 2H).

MS (ESIpos): m/z=512 (M+H)$^+$ c) 2-{2-[2-(4-{(E)-2-[4-(methylamino)phenyl]vinyl}phenoxy)ethoxy]-ethoxy}ethyl 4-methylbenzenesulfonate trifluoroacetate (2f)

200 mg 2-[2-(2-{4-[(E)-2-{4-[(tert-butoxycarbonyl)(methyl)amino]phenyl}-vinyl]phenoxy}ethoxy)ethoxy]ethyl 4-methylbenzenesulfonate (2c) were dissolved in 2.5 mL dichloromethane. 252 µL trifluoroacetic acid were added and the mixture was stirred for 5 h at room temperature. The solvent was removed under reduced pressure. The crude product was washed with hexane and diethyl ether and dried under reduced pressure 84 mg 2f were obtained as light brown solid.

$^1$H NMR (300 MHz, DMSO d6) δ ppm 2.40 (s, 3H), 2.72 (s, 3H), 3.46-3.50 (m, 2H), 3.51-3.55 (m, 2H), 3.57-3.61 (m, 2H), 3.69-3.73 (m, 2H), 4.10-4.09 (m, 2H), 4.10-4.13 (m, 2H),), 6.59-6.66 (m, 2H), 6.85-6.97 (m, 4H), 7.34 (d, J=8.3 Hz, 2H), 7.43 (d, J=8.8 Hz, 2H), 7.46 (d, J=8.1 Hz, 2H), 7.76 (d, J=8.3 Hz, 2H).

MS (ESIpos): m/z=512 (M+H)$^+$

Radiolabeling of 2-{2-[2-(4-{(E)-2-[4-(methylamino)phenyl]vinyl}phenoxy)ethoxy]-ethoxy}ethyl 4-methylbenzenesulfonates (2d, 2e, 2f)

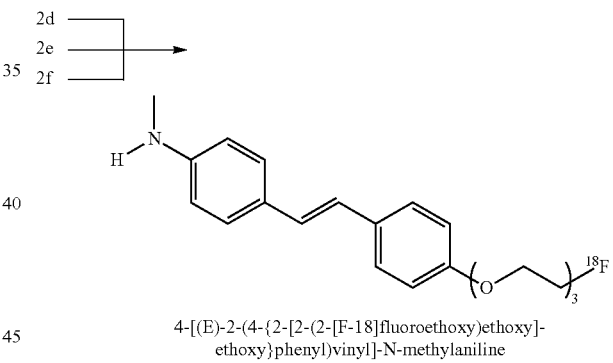

4-[(E)-2-(4-{2-[2-(2-[F-18]fluoroethoxy)ethoxy]-ethoxy}phenyl)vinyl]-N-methylaniline Radiolabelings have been performed using potassium carbonate/kryptofix. tetrabutylammonium hydroxide or tetrabutylammonium bicarbonate as reagent.

a) Radiolabeling with Potassium Carbonate/Kryptofix

[F-18]fluoride was trapped on a QMA cartridge. The activity was eluted using a solution of 7.5 mg kryptofix, 1 mg potassium carbonate in 1425 µL acetonitrile and 75 µL water. The mixture was dried under gentle nitrogen stream at 120° C. Drying was repeated after addition of 1 mL acetonitrile.

The precursor (5.0 mg 2d or 5.36 mg 2e or 6.11 mg 2f) in 1 mg acetonitrile was added and the mixture was heated at 120° C. for 15 min. Fluoride incorporation was measured by radio-TLC (silica, ethyl acetate), results as summarized in Table 4.

b) Radiolabeling with Tetrabutylammonium Hydroxide

[F-18]fluoride was trapped on a QMA cartridge. The activity was eluted using a mixture of 300 µL≈4% n-Bu$_4$OH and 600 µL acetonitrile. The mixture was dried under gentle nitrogen stream at 120° C. Drying was repeated after addition of 1 mL acetonitrile.

The precursor (5.0 mg 2d or 5.36 mg 2e or 6.11 mg 2f) in 1 mg acetonitrile was added and the mixture was heated at 120° C. for 15 min. Fluoride incorporation was measured by radio-TLC (silica, ethyl acetate), results as summarized in Table 4.

c) Radiolabeling with Tetrabutylammonium Bicarbonate

[F-18]fluoride was trapped on a QMA cartridge. The activity was eluted using a mixture of 300 µL≈4% n-Bu$_4$NHCO$_3$ (a aqueous solution of 4% n-Bu$_4$OH was saturated with carbon dioxide) and 600 µL acetonitrile. The mixture was dried under gentle nitrogen stream at 120° C. Drying was repeated after addition of 1 mL acetonitrile.

The precursor (5.0 mg 2d or 5.36 mg 2e or 6.11 mg 2f) in 1 mg acetonitrile was added and the mixture was heated at 120° C. for 15 min. Fluoride incorporation was measured by radio-TLC (silica, ethyl acetate), results as summarized in Table 4.

TABLE 4

Radiolabeling of 2d, 2e, 2f

| Precursor | Reagent | F-18 incorporation |
|---|---|---|
| 5.0 mg 2d | Potassium carbonate/kryptofix | 91% |
|  | n-Bu$_4$NOH | 26% |
|  | n-Bu$_4$NHCO$_3$ | 39% |
| 5.36 mg 2e | Potassium carbonate/kryptofix | 45% |
|  | n-Bu$_4$NOH | 18% |
|  | n-Bu$_4$NHCO$_3$ | 75% |
| 6.11 mg 2f | Potassium carbonate/kryptofix | 77% |
|  | n-Bu$_4$NOH | 21% |
|  | n-Bu$_4$NHCO$_3$ | 78% |

Example 5

Comparison of 4-[(E)-2-(4-{2-[2-(2-[F-18]fluoroethoxy)ethoxy]-ethoxy}phenyl)vinyl]-N-methylaniline Radiosynthesis on GE Tracerlab FX$_N$ Using 3.5 mg vs. 7 mg Mesylate Precursor 2a The synthesis of 4-[(E)-2-(4-{2-[2-(2-[F-18]fluoroethoxy)ethoxy]-ethoxy}phenyl)vinyl]-N-methylaniline have been performed on a Tracerlab FX$_N$ synthesizer (FIG. 1).

The setup of the synthesizer and the results are summarized in Table 5. [F-18]Fluoride was trapped on a QMA cartridge (C1, FIG. 1). The activity was eluted with potassium carbonate/kryptofix mixture (from "V1") into the reactor.

The solvent was removed while heating under gentle nitrogen stream and vacuum. Drying was repeated after addition of acetonitrile (from "V2"). The solution of 2a (from "V3") was added to the dried residue and the mixture was heated for 8 min at 120° C. After cooling to 60° C., HCl/acetonitrile mixture (from "V4") was added and solution was heated for 4 min at 110° C.

The crude product was transferred to the "Mix-Vial" and diluted with sodium hydroxide/ammonium formate mixture from "V6". The crude product was purified by semi-preparative HPLC. The product fraction was collected into the "Flask" containing 30 mL water. the solution was passed through a tC18 plus cartridge (C3). The cartridge was washed with 20% ethanol in water from "V9" and 4-[(E)-2-(4-{2-[2-(2-fluoroethoxy)ethoxy]-ethoxy}phenyl)vinyl]-N-methylaniline was eluted with 1.5 mL ethanol into the product vial containing 8.5 mL formulation basis (consisting of phosphate buffer, PEG400 and ascorbic acid).

TABLE 5

Setup of Tracerlab FX$_N$ for synthesis of 4-[(E)-2-(4-{2-[2-(2-[F-18]fluoroethoxy)ethoxy]-ethoxy}phenyl)vinyl]-N-methylaniline

|  | 3.5 mg precursor | 7.0 mg precursor |
|---|---|---|
| Vial V1 | 1.5 mg potassium carbonate, 5 mg kryptofix in 0.075 mL water and 1.425 mL acetonitrile | |
| Vial V2 | 1 mL acetonitrile for drying | |
| Vial V3 | 3.5 mg precursor 2a in 1 mL acetonitrile | 7 mg precursor 2a in 1 mL acetonitrile |
| Vial V4 | 0.5 mL 2M HCl and 0.5 mL acetonitrile | |
| Vial V6 | 1 mL 1M NaOH and 2 mL ammonium formate (0.1M) | |
| Vial V8 | 1.5 mL ethanol | |
| Vial V9 | 5 mL (20% ethanol in water) + 10 mg ascorbic acid | |
| Cartridge C1 | QMA light (Waters) | |
| Cartridge C3 | tC18 plus (Waters) | |
| Flask | 30 mL water + 60 mg ascorbic acid | |
| HPLC column | Zorbax Bonus RP, 9.4 * 250 mm; 5 µm; (Agilent) | |
| HPLC solvent | 55% acetonitrile, 45% ammonium formate (0.1M) | |
| HPLC flow | 4 mL/min | |
| Start activity of [F-18]fluoride | 54000 MBq | 36600 MBq |
| Product activity | 12600 MBq | 18000 MBq |
| Radiochemical yield | 23% (not corrected for decay) | 49% (not corrected for decay) |

Significant increase of radiochemical yield for 4-[(E)-2-(4-{2-[2-(2-[F-18]fluoroethoxy)ethoxy]-ethoxy}phenyl)vinyl]-N-methylaniline was found after increasing the amount of precursor from 3.5 mg to 7.0 mg.

Example 6

Comparison of 4-[(E)-2-(4-{2-[2-(2-[F-18]fluoroethoxy)ethoxy]-ethoxy}phenyl)vinyl]-N-methylaniline Radiosynthesis on Eckert & Ziegler ModularLab Using Acetonitrile Vs. Tert-Amyl Alcohol as Solvent for Radiofluorination The synthesis of 4-[(E)-2-(4-{2-[2-(2-fluoroethoxy)ethoxy]-ethoxy}phenyl)vinyl]-N-methylaniline has been performed on Eckert & Ziegler ModularLab synthesizer using acetonitrile or tert-amyl alcohol as solvent for fluorination. The setup of the synthesizer and the results are summarized in the Table below.

[F-18]Fluoride was trapped on a QMA cartridge (C1). The activity was eluted with a kryptofix mixture (from "V1") into the reactor. The solvent was removed while heating under gentle nitrogen stream and vacuum. Drying was repeated after addition of acetonitrile (from "V2"). The solution of precursor 2a (from "V3") was added to the dried residue and the mixture was heated for 12 min at 120° C. The solvent of fluorination was removed under vacuum for 6 min at 120° C. After cooling to 40° C., HCl/acetonitrile mixture (from "V4") was added and solution was heated for 10 min at 120° C.

The crude product mixture was diluted with 1.5 mL 2M NaOH and 0.3 mL ammonium formate (1M) from "V5" and then directly transferred to the HPLC vial ("Mix-Vial"). To avoid the precipitation and the phase separation of the mixture due to the tert-amyl alcohol, the "Mix-Vial" contained previously 1 mL acetonitrile and 1 mL ethanol. In contrast, it was found that no additional organic solvents was necessary in the "Mix-Vial" if acetonitrile is used as solvent for fluorination.

The mixture was purified by semi-preparative HPLC. The product fraction was collected into the "Flask" containing 16 mL water. The solution was passed through a tC18 environmental cartridge (C2). The cartridge was washed with 20% ethanol in water from "V6" and 4-[(E)-2-(4-{2-[2-(2-fluoroethoxy)ethoxy]-ethoxy}phenyl)vinyl]-N-methylaniline was eluted with 1.5 mL ethanol from "V7" into the product vial containing 8.5 mL formulation basis (consisting of phosphate buffer, PEG400 and ascorbic acid).

A higher radiochemical yield of 48% (not corrected for decay) was obtained using 8 mg precursor in 1.8 mL acetonitrile compared to the process using 7.4 mg precursor in 1 mL tert-amyl alcohol that afforded 38% (not corrected for decay) 4-[(E)-2-(4-{2-[2-(2-[F-18]fluoroethoxy)ethoxy]-ethoxy}phenyl)vinyl]-N-methylaniline.

[F-18]Fluoride was trapped on a QMA cartridge (C1). The activity was eluted with a kryptofix mixture (from "V1") into the reactor. The solvent was removed while heating under gentle nitrogen stream and vacuum. Drying was repeated is after addition of acetonitrile (from "V2"). The solution of precursor 2a (from "V3") was added to the dried residue and the mixture was heated for 10 min at 120° C. The solvent of fluorination was removed under vacuum for 6 min at 120° C. if tert-amyl alcohol is used as solvent for fluorination. No evaporation step was necessary when acetonitrile is used as solvent for fluorination. After cooling to 40° C., HCl/acetonitrile mixture (from "V4") was added and solution was heated for 7 min at 100° C. if tert-amyl alcohol is used as solvent for fluorination, and for 5 min at 110° C. if acetonitrile is used as solvent for fluorination.

|  | Radiolabeling in tert-amyl alcohol | Radiolabeling in acetonitrile |
| --- | --- | --- |
| Vial V1 | 22 mg kryptofix<br>700 µL methanol<br>10 µL tert-butyl ammonium carbonate 40%<br>100 µL potassium mesylate 0.2M | 22 mg kryptofix<br>7 mg potassium carbonate<br>300 µL acetonitrile<br>300 µL water |
| Vial V2 | 100 µL acetonitrile for drying | |
| Vial V3 | 7.4 mg precursor 2a in 140 µL acetonitrile and 1.0 mL tert-amyl alcohol | 8.0 mg precursor 2a in 1.8 mL acetonitrile |
| Vial V4 | 2 mL HCl 1.5M<br>1 mL acetonitrile<br>30 mg sodium ascorbate | |
| Vial V5 | 1.5 mL NaOH 2.0M<br>300 µL ammonium formate 1M<br>500 µL ethanol | |
| Vial V6 | 8 mL ethanol 20%<br>80 mg sodium ascorbate | |
| Vial V7 | 1.5 mL ethanol | |
| Cartridge C1 | QMA light (waters) conditioned with potassium mesylate 0.2M | QMA light (waters) conditioned with potassium carbonate 0.5M |
| Cartridge C2 | tC18 environmental (Waters) | |
| Mix-Vial | 1 mL acetonitrile<br>1 mL ethanol | — |
| Flask | 16 mL water<br>160 mg sodium ascorbate | |
| HPLC column | Gemini C18, 10 * 250 mm, 5 µm, Phenomenex | |
| HPLC solvent | 60% acetonitrile, 40% phosphate buffer 50 mM pH 4 | 70% acetonitrile, 30% ammonium formate buffer 0.1M with 5 mg/mL sodium ascorbate |
| HPLC flow | 3 mL/min | |
| Start activity of [F-18]fluoride | 30.4 GBq | 33.8 GBq |
| Product activity | 11.6 GBq | 16.2 GBq |
| Process time | 72 min | 71 min |
| Product purity (RCP) | 99.0% | 99.3% |
| Radiochemical yield | 38% (not corrected for decay) | 48% (not corrected for decay) |

Example 7

Comparison of 4-[(E)-2-(4-{2-[2-(2-[F-18]fluoroethoxy)ethoxy]-ethoxy}phenyl)vinyl]-N-methylaniline Radiosynthesis on GE Tracerlab MX Using Acetonitrile vs. Tert-Amyl Alcohol as Solvent for Radiofluorination The synthesis of 4-[(E)-2-(4-{2-[2-(2-fluoroethoxy)ethoxy]-ethoxy}phenyl)vinyl]-N-methylaniline has been performed on GE TracerLab MX synthesizer using acetonitrile or tert-amyl alcohol as solvent for fluorination. The setup of the synthesizer and the results are summarized in the Table below.

The crude product mixture was diluted with 1.8 mL 2M NaOH and 0.3 mL ammonium formate (1M) from "V5" and then directly transferred to the product vial containing 0.5 mL ethanol.

A higher radiochemical yield of 73% (not corrected for decay) was obtained using 8 mg precursor in 1.8 mL acetonitrile compared to the process using 8 mg precursor in 1.7 mL tert-amyl alcohol and 0.4 mL acetonitrile that afforded 66% is (not corrected for decay) for the not purified 4-[(E)-2-(4-{2-[2-(2-[F-18]fluoroethoxy)ethoxy]-ethoxy}phenyl)vinyl]-N-methylaniline.

|  | Radiolabeling in tert-amyl alcohol | Radiolabeling in acetonitrile |
| --- | --- | --- |
| Vial V1 | 22 mg kryptofix<br>700 µL methanol<br>10 µL tert-butyl ammonium carbonate 40%<br>100 µL potassium mesylate 0.2M | 22 mg kryptofix<br>7 mg potassium carbonate<br>300 µL acetonitrile<br>300 µL water |
| Vial V2 | 8 mL acetonitrile | |
| Vial V3 | 8 mg precursor 2a in 400 µL acetonitrile and 1.7 mL tert-amyl alcohol | 8 mg precursor 2a in 1.8 mL acetonitrile |
| Vial V4 | 2.2 mL HCl 1.5M<br>1.1 mL acetonitrile<br>30 mg sodium ascorbate | |
| Vial V5 | 1.8 mL NaOH 2.0M<br>300 µL ammonium formate 1M | |
| Product vial | 500 µL ethanol | |
| Cartridge C1 | QMA light (waters) conditioned with potassium mesylate 0.2M | QMA light (waters) conditioned with potassium carbonate 0.5M |
| Start activity of [F-18]fluoride | 94.7 GBq | 173.1 GBq |
| Product activity | 75.1 GBq | 148.0 GBq |
| Process time | 46 min | 30 min |
| Recovery Raw batch | 79% (not corrected for decay) | 85% (not corrected for decay) |
| Purity Raw batch (TLC) | 77% | 100% |
| Radiochemical yield | 61% (not corrected for decay) | 85% (not corrected for decay) |

An additional advantage of the process wherein acetonitrile is used instead of tert-amyl alcohol is pattern of the radiochemical purity of the raw batch.

The radiolabeling time is shorter when acetonitrile is used as solvent for fluorination since no evaporation of solvent is necessary after radiolabeling as with tert-amyl alcohol solvent. Additionally a significant reduction of radioactivity losses is observed with acetonitrile as solvent for fluorination due to the absence of residual activity in the vacuum line occurring during the evaporation step of the process with tert-amyl alcohol.

Example 8

Comparison of Process in DMSO and New Process in Acetonitrile

A series of 4-[(E)-2-(4-{2-[2-(2-[F-18]fluoroethoxy)ethoxy]-ethoxy}phenyl)vinyl]-N-methylaniline syntheses was performed on three different synthesizers (Eckert & Ziegler modular lab, GE tracerlab FX, GE tracerlab MX) as generally described by WO2006066104, Zhang et al., Example 1, Example 6 and Example 7. The crude product mixtures were purified by HPLC method A or B.

Method A): The crude product mixture obtained after deprotection is neutralized with a mixture of 2M NaOH and 0.1M ammonium formate (for labelings in DMSO, the crude mixture was additionally pre-purified by solid-phase extraction on a C18 light cartridge, prior loading onto HPLC) and injected onto a semipreparative HPLC (e.g. column: Gemini C18, 10×250 mm, 5 µm, Phenomenex; solvent: 70% acetonitrile, 30% ammonium formate buffer 0.1M with 5 mg/mL sodium ascorbate, flow rate 3 mL/min). The product fraction is collected into a flask containing approx. 160 mL water with 10 mg/mL sodium ascorbate. The mixture is passed through a C18 cartridge (tC18 SepPak environmental, Waters). The cartridge is washed with approx. 8-10 mL 20% EtOH in water (containing 10 mg/mL sodium ascorbate). Finally, the product is eluted with 1.5 or 3 mL ethanol into a vial containing 8.5 or 17 mL "Formulation basis" (comprising PEG400, phosphate buffer and ascorbic acid).

Method B): (not used for radiolabelings in DMSO) The crude product mixture obtained after deprotection is neutralized with a mixture of 2M NaOH and 0.1M ammonium formate and injected onto a semipreparative HPLC (column: e.g.: Gemini C18, 10×250 mm, 5 µm, Phenomenex or Synergi Hydro-RP, 250×10 mm, 10 µm 80 Å, Phenomenex or Synergi Hydro-RP, 250×10 mm, 4 µm 80 Å, Phenomenex; solvent: 60-70% ethanol, 40-30% ascorbate buffer≈5 mg/mL ascorbate; flow 3 mL/min or 4 mL/min or 6 mL/min). The product fraction is is directly collected into a vial containing "Formulation basis" (comprising PEG400, phosphate buffer and ascorbic acid) to provide 10-24 mL of the final Formulation. The peak-cutting time was adjusted in the software to obtain a Formulation comprising 15% EtOH.

Every empty square (each one a result for one synthesis using DMSO, 8 experiments) and every filled dot (each one a result for a synthesis using acetonitrile, 108 experiments) in FIG. 9 represents an individual experiment for the manufacturing of 4-[(E)-2-(4-{2-[2-(2-[F-18]fluoroethoxy)ethoxy]-ethoxy}phenyl)vinyl]-N-methylaniline. The tendency of product activity in correlation with starting activity of [F-18]fluoride is illustrated by trendlines.

An almost linear correlation of product activity to starting activity is demonstrated for the new process of the present invention using acetonitrile. In contrast, lower yields are obtained by using DMSO as reaction solvent, especially at high lever of radioactivity.

Example 9

Comparison of Process in Tert-Alcohol Process and New Process in Acetonitrile

A series of 4-[(E)-2-(4-{2-[2-(2-[F-18]fluoroethoxy)ethoxy]-ethoxy}phenyl)vinyl]-N-methylaniline syntheses was performed on two different synthesizers (Eckert & Ziegler modular lab and GE tracerlab MX) as generally described by US20100113763, Example 6 and Example 7. The crude product mixtures were purified by HPLC method A or B:

Method A):

The crude product mixture obtained after deprotection is neutralized with a mixture of 2M NaOH and 0.1M ammonium formate and injected onto a semipreparative HPLC (e.g. column: Gemini C18, 10×250 mm, 5 µm, Phenomenex; solvent: 70% acetonitrile, 30% ammonium formate buffer 0.1M with 5 mg/mL sodium ascorbate, flow rate 3 mL/min). The product fraction is collected into a flask containing approx. 160 mL water with 10 mg/mL sodium ascorbate. The mixture is passed through a C18 cartridge (tC18 SepPak environmental, Waters). The cartridge is washed with approx. 8-10 mL 20% EtOH in water (containing 10 mg/mL sodium ascorbate). Finally, the product is eluted with 1.5 or 3 mL ethanol into a vial containing 8.5 or 17 mL "Formulation is basis" (comprising PEG400, phosphate buffer and ascorbic acid).

Method B):

The crude product mixture obtained after deprotection is neutralized with a mixture of 2M NaOH and 0.1M ammonium formate and injected onto a semipreparative HPLC (column: e.g.: Gemini C18, 10×250 mm, 5 µm, Phenomenex or Synergi Hydro-RP, 250×10 mm, 10 µm 80 Å, Phenomenex or Synergi Hydro-RP, 250×10 mm, 4 µm 80 Å, Phenomenex; solvent: 60-70% ethanol, 40-30% ascorbate buffer≈5 mg/mL ascorbate; flow 3 mL/min or 4 mL/min or 6 mL/min). The product fraction is directly collected into a vial containing "Formulation basis" (comprising PEG400, phosphate buffer and ascorbic acid) to provide 10-24 mL of the final Formulation. The peak-cutting time was adjusted in the software to obtain a Formulation comprising 15% EtOH.

Every cross (each one result for a synthesis comprising using tert-amylalcohol, 103 experiments) and every filled dot (each one result for a synthesis using acetonitrile, 108 experiments) in FIG. 10 represents an individual experiment for the manufacturing of 4-[(E)-2-(4-{2-[2-(2-[F-18]fluoroethoxy)ethoxy]-ethoxy}phenyl)vinyl]-N-methylaniline. The tendency of product activity in correlation with starting activity of [F-18]fluoride is illustrated by trendlines.

An almost linear correlation is found for the results of the new process of the present invention using acetonitrile. In contrast, a higher variation of results and lower yields—especially at higher levels of radioactivity—are obtained by using tert-amylalcohol as reaction solvent.

Example 10

Synthesis of 4-[(E)-2-(6-{2-[2-(2-[F-18]fluoroethoxy)ethoxy]-ethoxy}pyridin-3-yl)vinyl]-N-methylaniline on Tracerlab FX$_N$ The synthesis was performed on a Tracerlab FX$_N$ synthesizer. [F-18]Fluoride (10 GBq) was trapped on a QMA cartridge. The activity was eluted with potassium carbonate/kryptofix/acetonitrile/water mixture into the reactor. The solvent was removed while heating under gentle nitrogen stream and vacuum. Drying was repeated after addition of acetonitrile. A solution of 8 mg 2b in 1.5 mL acetonitrile is was added to the dried residue and the mixture was heated for 10 min at 120° C. After cooling to 60° C., 1 mL 1.5M HCl was added and the reactor was heated at 110° C. for 5 min. The crude product was neutralized (1 mL 1M NaOH/ammonium formate), diluted (with 0.5 mL EtOH and 1.5 mL MeCN) and transferred to a semi-preparative HPLC column (Synergy Hydro-RP, 250×10 mm, Phenomenex). A mixture of 60% ethanol and 40% ascorbate buffer (5 g/l sodium ascorbate and 50 mg/l ascorbic acid, pH 7.0) was flushed through the column with 3 mL/min. The product fraction at ≈10 min was directly collected for 100 sec and mixed with 15 mL Formulation basis (phosphate buffer, ascorbic acid, PEG400).

4.2 GBq (42% not corrected for decay) were obtained in 61 min overall synthesis time. Radiochemical purity (determined by HPLC, $t_R$=3.42 min) was determined to be >99%.

Example 11

Synthesis of 4-[(E)-2-(4-{2-[2-(2-[F-18]fluoroethoxy)ethoxy]-ethoxy}phenyl)vinyl]-N-methylaniline on Tracerlab FX$_N$

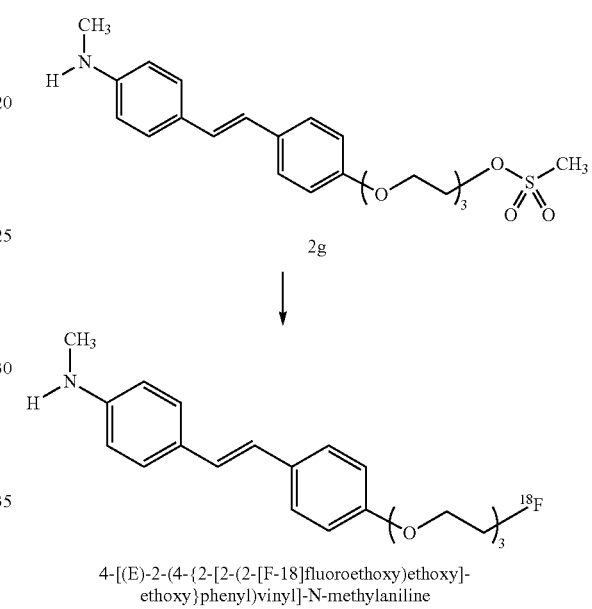

4-[(E)-2-(4-{2-[2-(2-[F-18]fluoroethoxy)ethoxy]-ethoxy}phenyl)vinyl]-N-methylaniline The synthesis was performed on a Tracerlab FX$_N$ synthesizer. [F-18]Fluoride (6.85 GBq) was trapped on a QMA cartridge. The activity was eluted with potassium carbonate/kryptofix/acetonitrile/water mixture into the reactor. The solvent was removed while heating under gentle nitrogen stream and vacuum. Drying was repeated after addition of acetonitrile. A solution of 8 mg 2 g in 1.5 mL acetonitrile was added to the dried residue and the mixture was heated for 10 min at 120° C. After cooling to 60° C., the crude product was diluted with 4 mL HPLC eluent and transferred to a semi-preparative HPLC column (Synergy Hydro-RP, 250×10 mm, Phenomenex). A mixture of 60% ethanol and 40% ascorbate buffer (5 g/l sodium ascorbate and 50 mg/l ascorbic acid, pH 7.0) was flushed through the column with 3 mL/min. The product fraction at ≈12 min was directly collected for 100 sec and mixed with 15 mL Formulation basis (phosphate buffer, ascorbic acid, PEG400).

2.54 GBq (37% not corrected for decay) were obtained in 53 min overall synthesis time. Radiochemical purity (determined by HPLC, $t_R$=3.78 min) was determined to be >99%.

Figure 1:
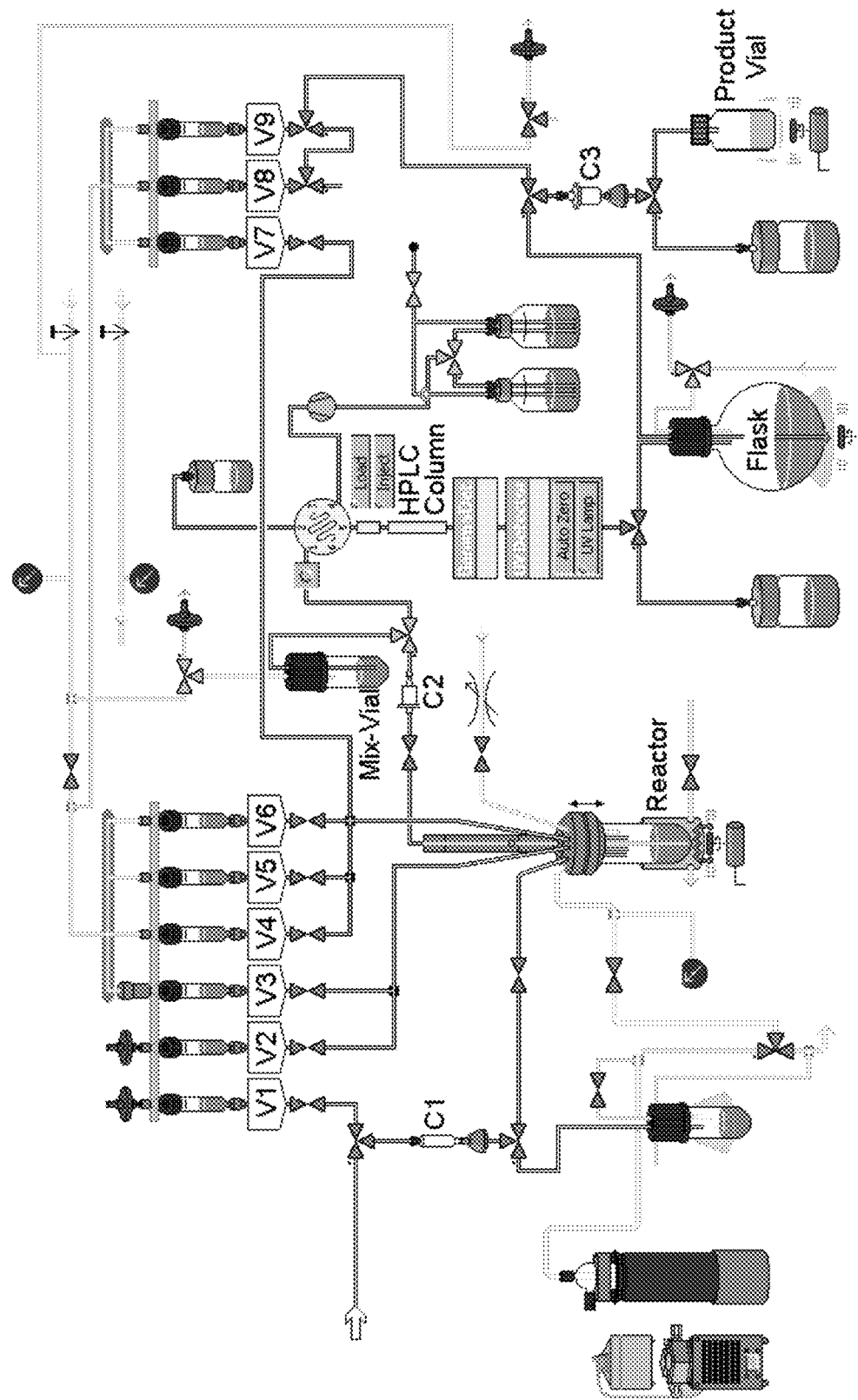
FIG. 1 Setup of Tracerlab FX$_N$ (adopted from tracerlab software)
Figure 2:
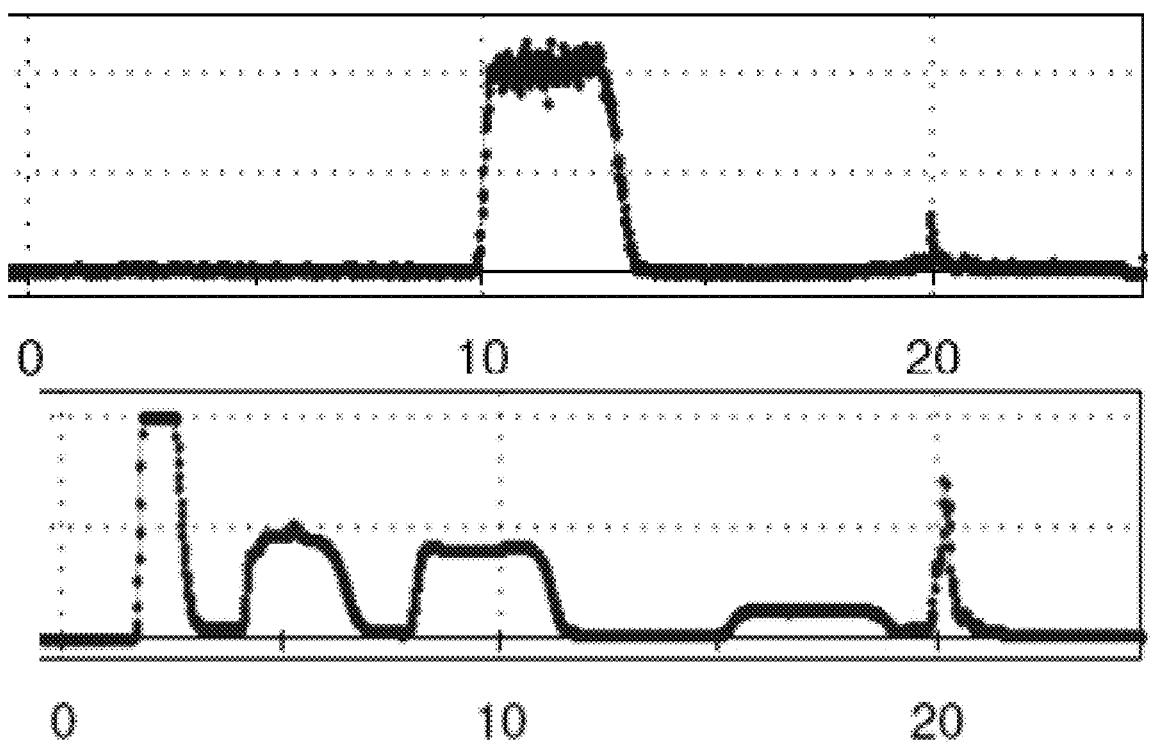
FIG. 2 preparative HPLC chromatogram of synthesis in DMSO (top: radioactivity, bottom: UV 254 nm)
Figure 3:
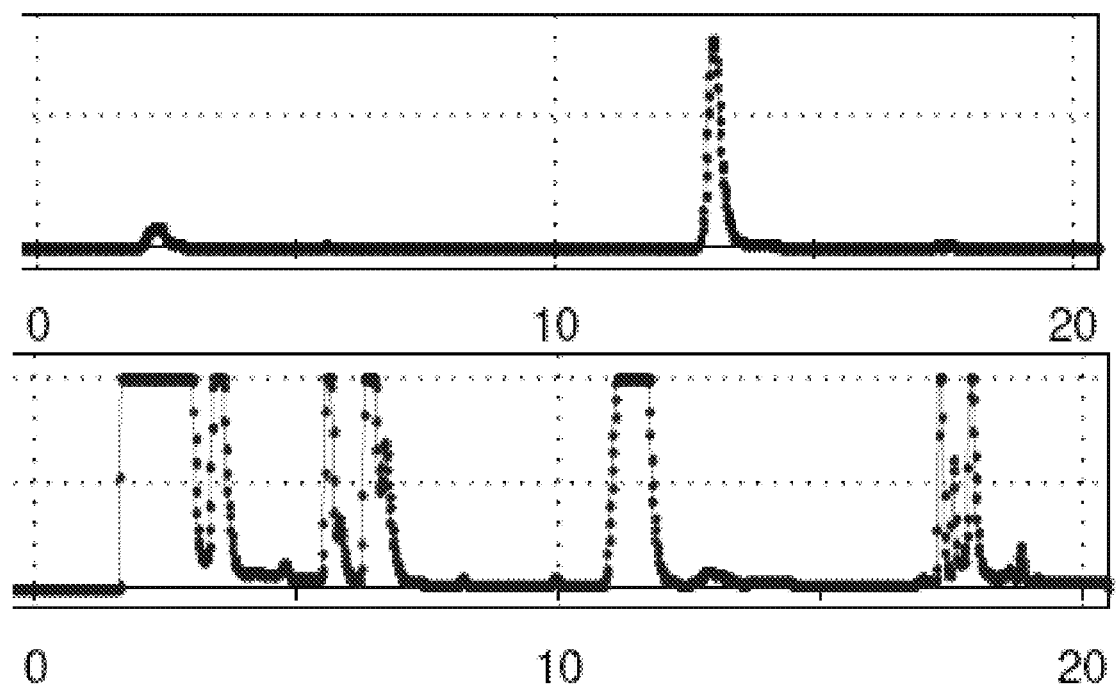
FIG. 3 preparative HPLC chromatogram of synthesis in acetonitrile (top: radioactivity, bottom: UV 254 nm)
Figure 4:
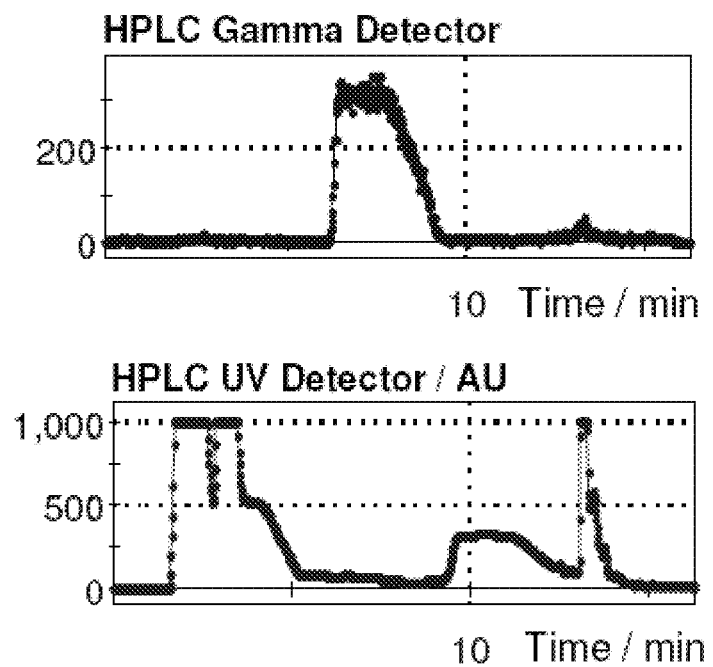
FIG. 4 preparative HPLC chromatogram of synthesis in DMSO (top: radioactivity, bottom: UV 254 nm)
Figure 5:
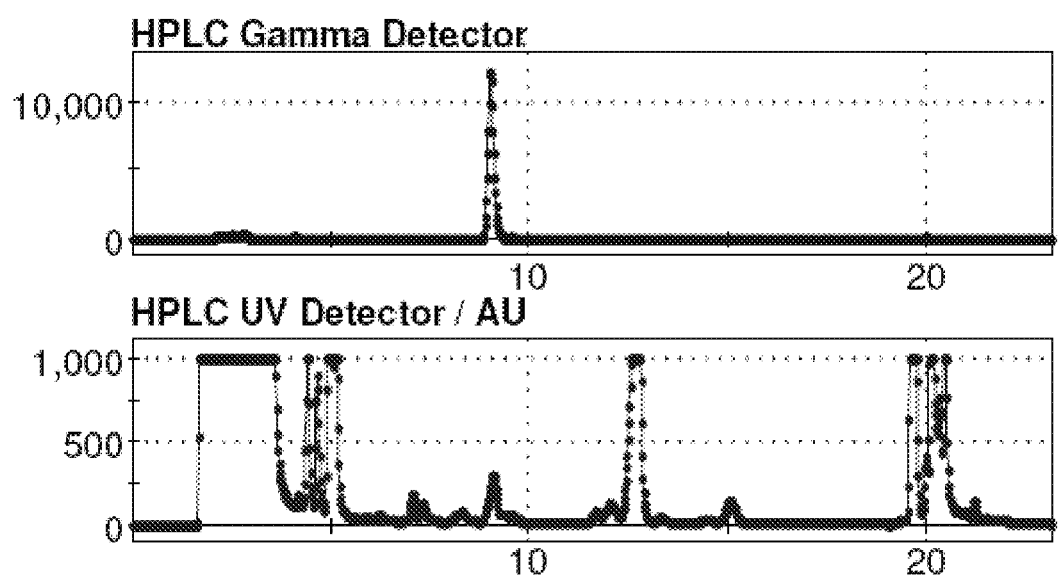
FIG. 5 preparative HPLC chromatogram of synthesis in acetonitrile (top: radioactivity, bottom: UV 254 nm)
Figure 6:
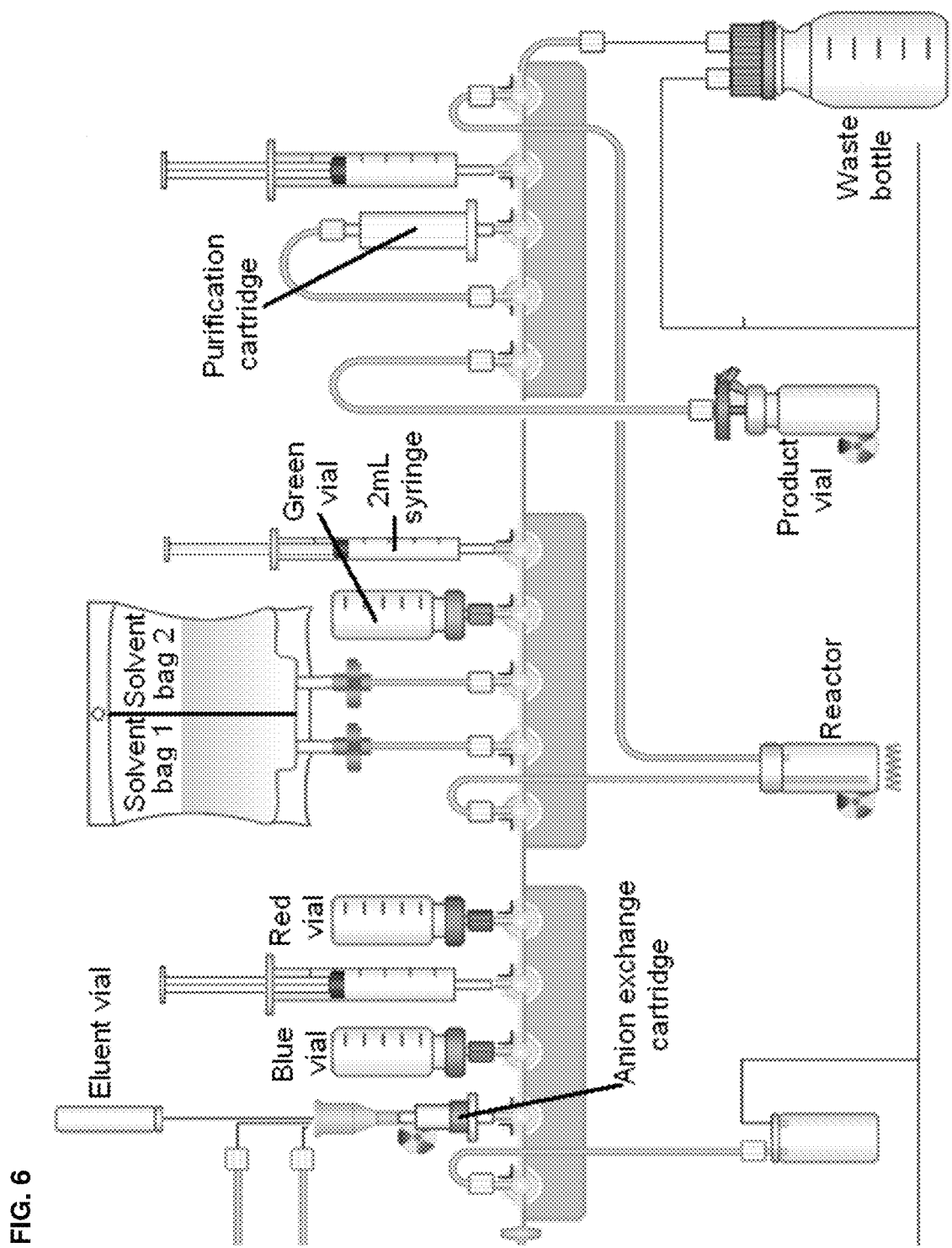
FIG. 6 Setup of Tracerlab MX for 4-[(E)-2-(4-{2-[2-(2-[F-18]fluoroethoxy)ethoxy]-ethoxy}phenyl)vinyl]-N-methyla-niline synthesis (adopted from coincidence FDG software)
Figure 7A:
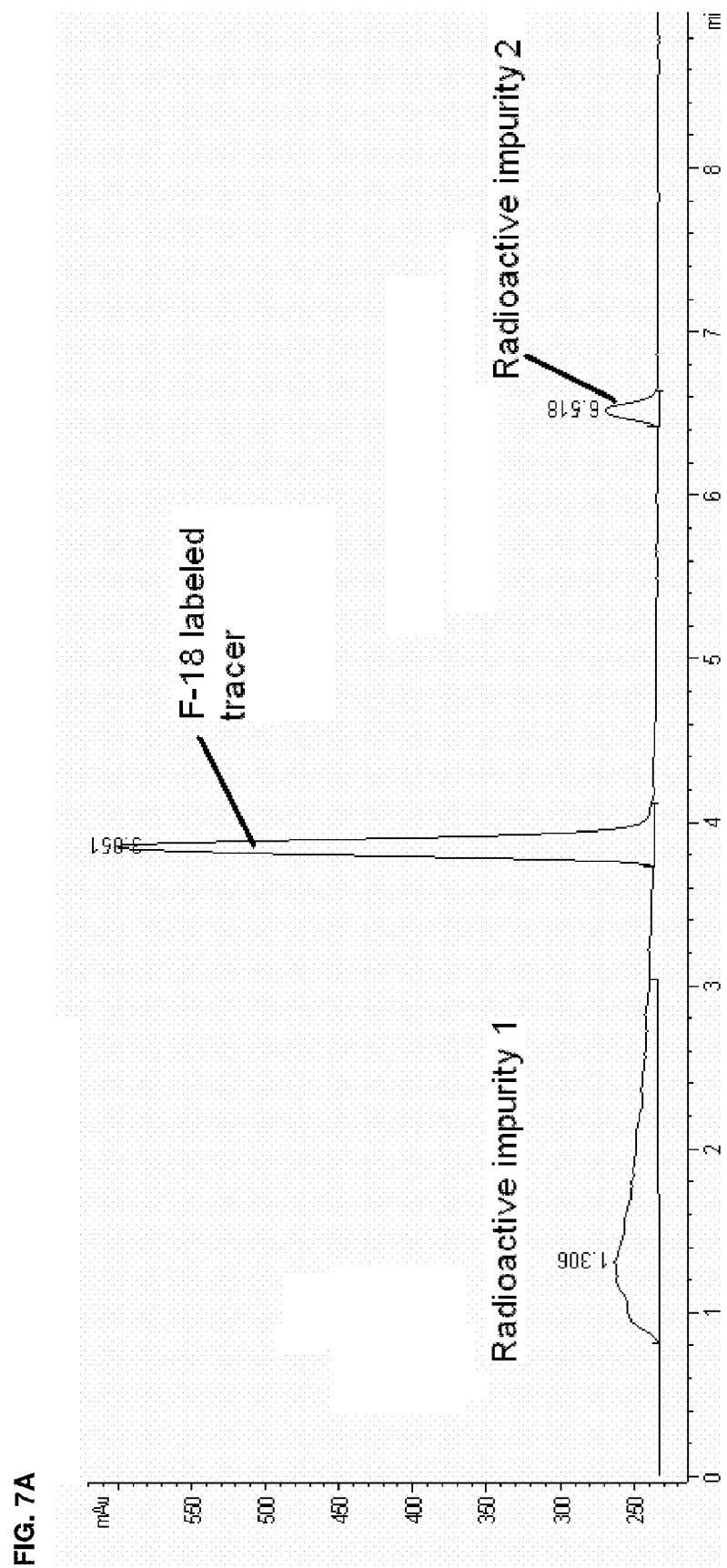
FIG. 7 Analytical HPLC of rude product of MX synthesis prior passing through "Purification cartridge" (sample was taken from reactor); a: radioactivity; b: UV signal 320 nm FIG. 8 Analytical HPLC of 4-[(E)-2-(4-{2-[2-(2-[F-18]fluoroethoxy)ethoxy]-ethoxy}phenyl)vinyl]-N-methyla-niline after MX synthesis and cartridge based purification; a: radioactivity; b: UV signal 320 nm FIG. 9 Comparison of results of new method (MeCN) with previous described method 1 (DMSO)
Figure 7B:
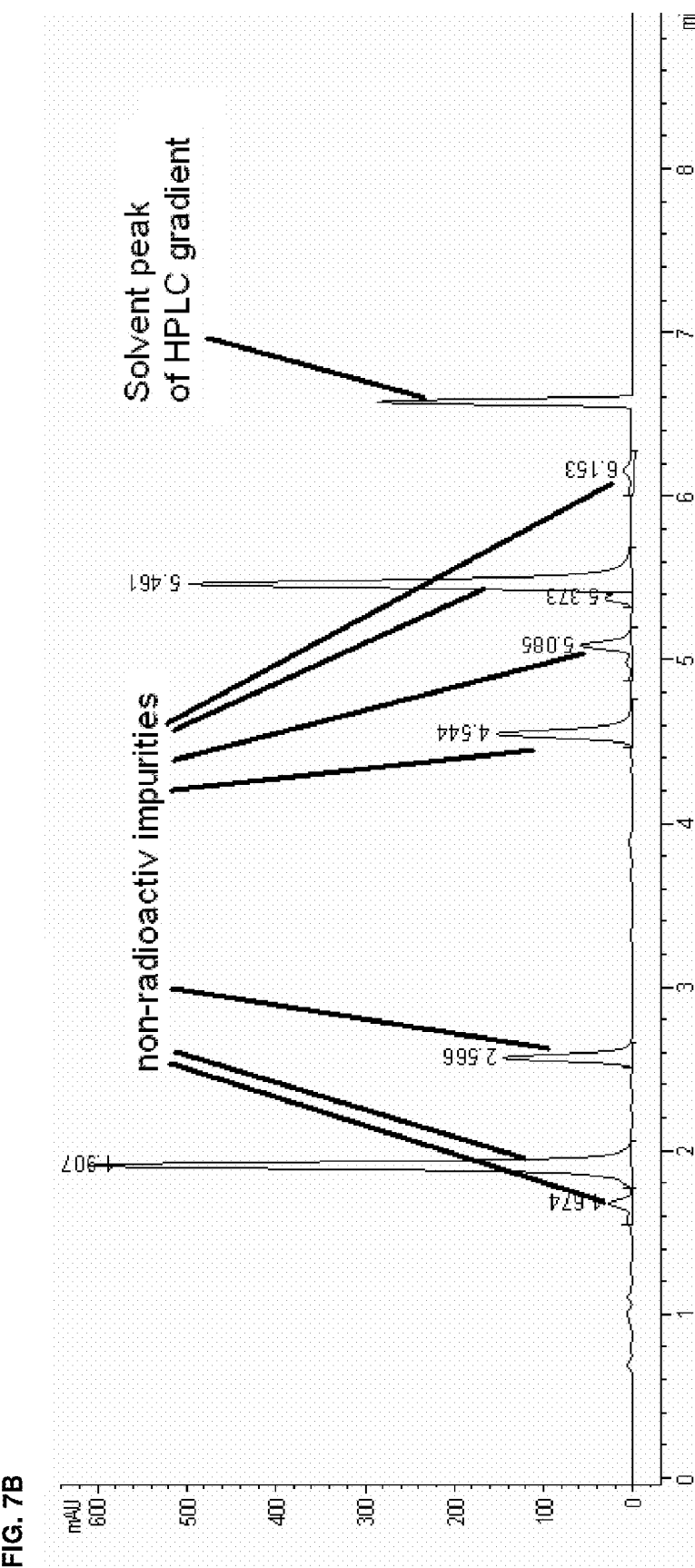
Figure 8A:
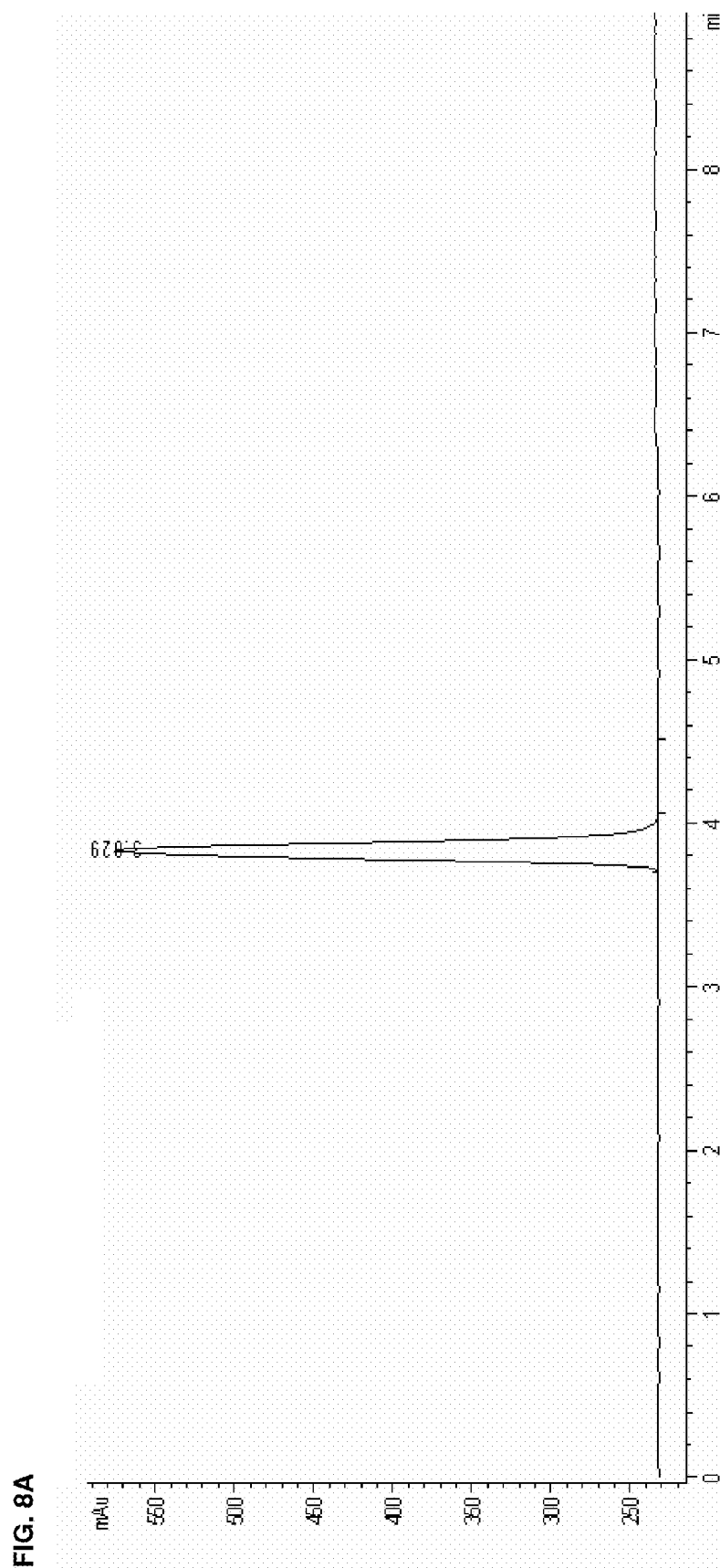
Figure 9:
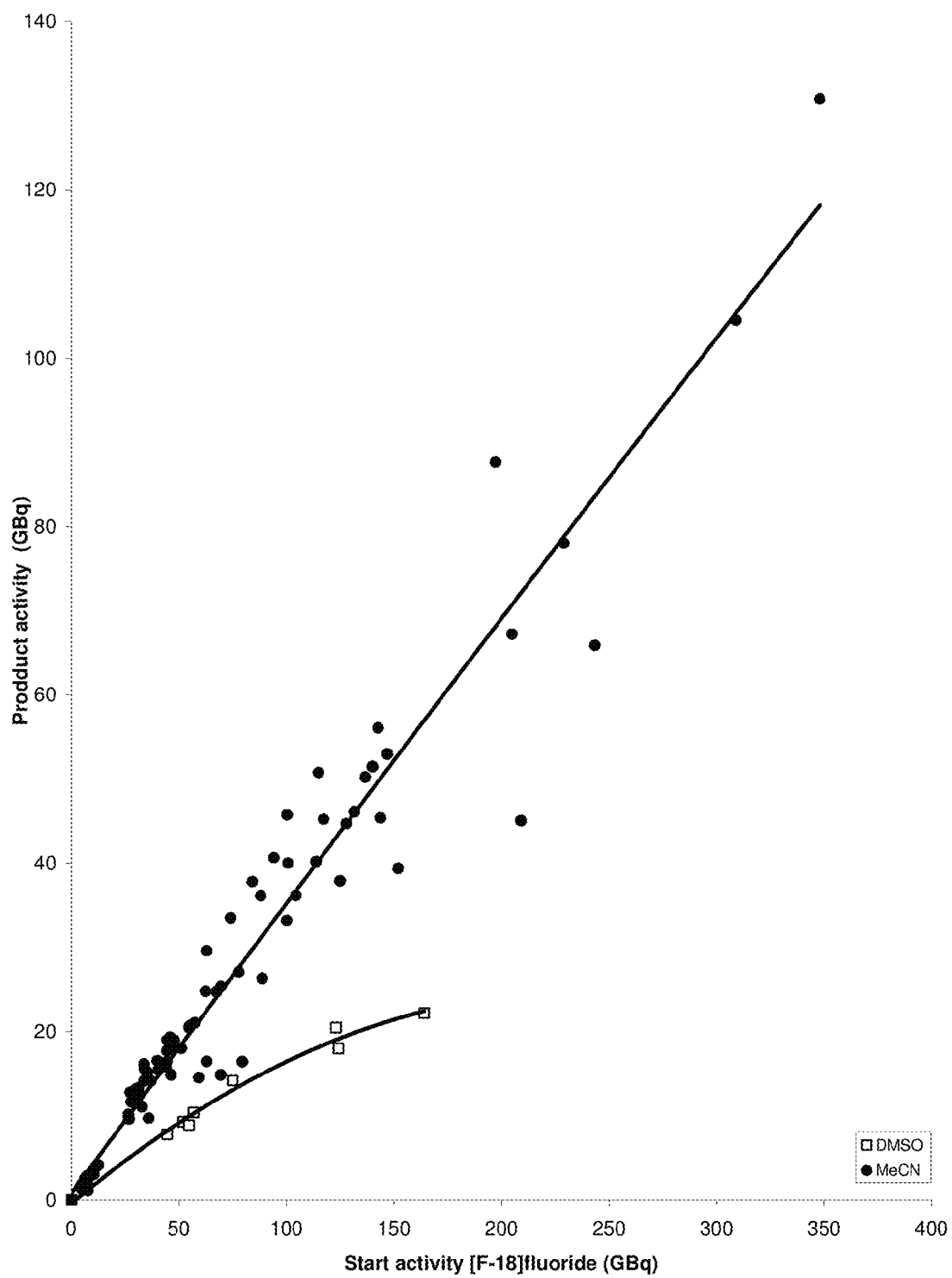
Figure 10:
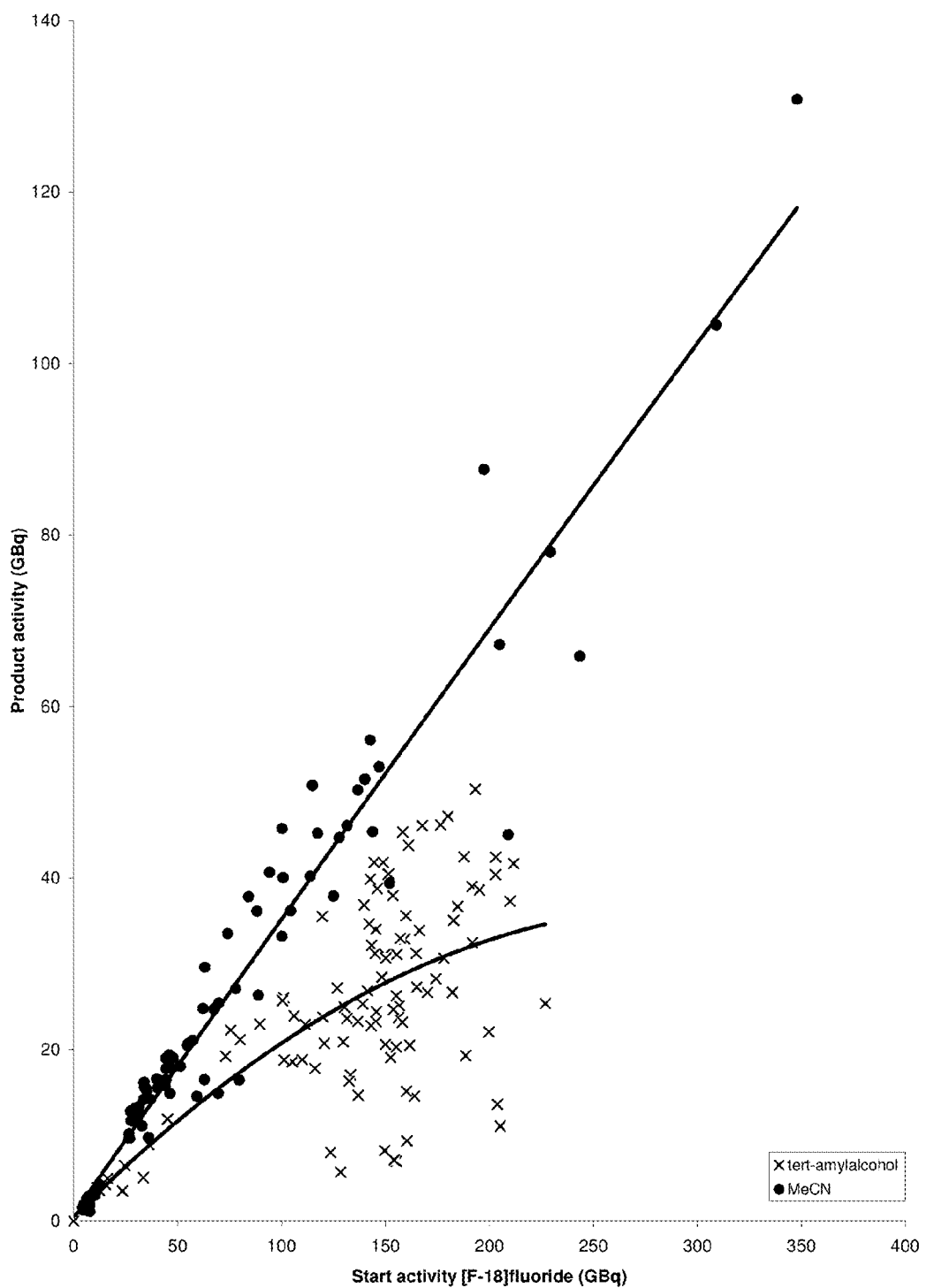
FIG. 10 Comparison of results of new method (MeCN) with previous described method 2 (tert-amylalcohol)

The invention claimed is:

1. A method for producing a compound of Formula I

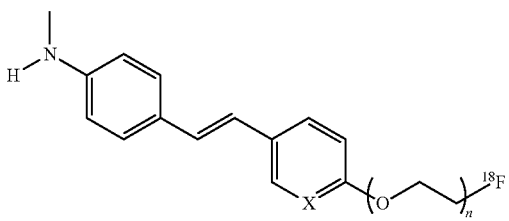

I comprising the steps of:
Step 1: radiolabeling a compound of Formula II with a F-18 fluorinating agent, to obtain a compound of Formula I, if R=H, or to obtain a compound of Formula III, if R=PG,

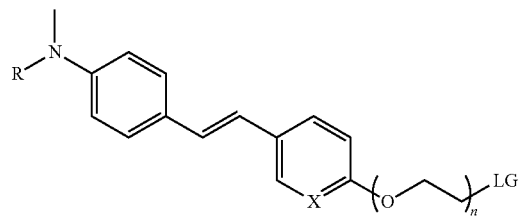

II

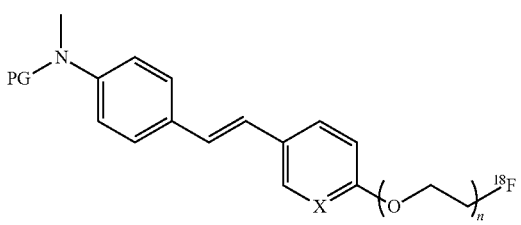

III wherein the radiolabeling is carried out in a mixture of acetonitrile and a co-solvent, wherein the percentage of acetonitrile is at least 50%,
Step 2: if R=PG, cleavage of the protecting group PG to obtain a compound of Formula I, and
Step 3: purification of a compound of Formula I,
wherein:
n=1-6,
selected from the group consisting of: a) CH, and b) N,
R is selected from the group consisting of: a) H, and b) PG,
PG is an amine-protecting group,
LG is a leaving group, wherein LG contains 0-3 fluorine atoms.

2. A method according to claim 1, wherein PG is selected from the group consisting of:
a) Boc,
b) trityl and
c) 4-methoxytrityl.

3. A method according to claim 1, wherein LG is selected from the group consisting of:
a) a halogen and
b) a sulfonyloxy,
wherein the halogen is chloro, bromo or iodo.

4. A method according to claim 3, wherein the sulfonyloxy is selected from the group consisting of:
a) methanesulfonyloxy,
b) p-toluenesulfonyloxy,
c) (4-nitrophenyl)sulfonyloxy, and
d) (4-bromophenyl)sulfonyloxy.

5. A method according to claim 1, wherein n=3 and X=CH.

6. A method according to claim 1, wherein n=3, X=CH, R=Boc, and LG=methanesulfonyloxy.

7. A method according to claim 1, wherein the radiolabeling is carried out in a mixture of acetonitrile and co-solvents, wherein the percentage of acetonitrile is at least 70%.

8. A method according to claim 1, wherein the radiolabeling is carried out in a mixture of acetonitrile and co-solvents, wherein the percentage of acetonitrile is at least 90%.

9. A method according to claim 1, wherein 1.5-75 µmol of a compound of Formula II are used in Step 1.

10. A method according claim 1, wherein the method is performed as a fully automated process.

11. A method according to claim 1, wherein Step 3 comprises a purification by HPLC.

12. A method according to claim 11, wherein the purification by HPLC in Step 3 employs a solvent which is a mixture of ethanol and an aqueous buffer.

13. A method according to claim 12, wherein the aqueous buffer comprises ascorbic acid or a salt thereof.

14. A method according to claim 1, wherein 10-30 µmol of a compound of Formula II are used in Step 1.

15. A method according to claim 1, wherein 12-25 µmol of a compound of Formula II are used in Step 1.

* * * * *

UNITED STATES PATENT AND TRADEMARK OFFICE
CERTIFICATE OF CORRECTION

| | |
|---|---|
| PATENT NO. | : 8,981,156 B2 |
| APPLICATION NO. | : 13/701595 |
| DATED | : March 17, 2015 |
| INVENTOR(S) | : Mathias Berndt et al. |

It is certified that error appears in the above-identified patent and that said Letters Patent is hereby corrected as shown below:

IN THE CLAIMS:

Column 36, line 9 (Claim 1), reads: -- selected from the group consisting of: a) CH, and b) N, --
Should read: -- X is selected from the group consisting of: a) CH, and b) N, --.

Signed and Sealed this
Twenty-fifth Day of August, 2015

Michelle K. Lee
*Director of the United States Patent and Trademark Office*